US012799474B2

(12) United States Patent
Ragland et al.

(10) Patent No.: US 12,799,474 B2
(45) Date of Patent: Nov. 17, 2026

(54) PURIFICATION OF SULFONATED DNA

(71) Applicant: Exact Sciences Corporation, Madison, WI (US)

(72) Inventors: Evan M. Ragland, Middleton, WI (US); Zubin Gagrat, Madison, WI (US); Michael J. Domanico, Middleton, WI (US)

(73) Assignee: Exact Sciences Corporation, Madison, WI (US)

( * ) Notice: Subject to any disclaimer, the term of this patent is extended or adjusted under 35 U.S.C. 154(b) by 655 days.

(21) Appl. No.: 18/005,943

(22) PCT Filed: Jul. 29, 2021

(86) PCT No.: PCT/US2021/043769
§ 371 (c)(1),
(2) Date: Jan. 18, 2023

(87) PCT Pub. No.: WO2022/039904
PCT Pub. Date: Feb. 24, 2022

(65) Prior Publication Data

US 2024/0026341 A1 Jan. 25, 2024

Related U.S. Application Data

(60) Provisional application No. 63/058,179, filed on Jul. 29, 2020.

(51) Int. Cl.
*C12N 15/10* (2006.01)

(52) U.S. Cl.
CPC ................................ *C12N 15/1013* (2013.01)

(58) Field of Classification Search
CPC ................................................. C12N 15/1013
USPC ......................................................... 536/25.4
See application file for complete search history.

(56) References Cited

U.S. PATENT DOCUMENTS

| | | | |
|---|---|---|---|
| 4,554,088 A | 11/1985 | Whitehead et al. | |
| 5,647,994 A | 7/1997 | Tuunanen et al. | |
| 5,648,124 A | 7/1997 | Sutor | |
| 5,663,242 A | 9/1997 | Ghosh et al. | |
| 5,702,950 A | 12/1997 | Tajima | |
| 5,786,146 A | 7/1998 | Herman et al. | |
| 6,194,562 B1 | 2/2001 | Smith et al. | |
| 6,270,970 B1 | 8/2001 | Smith et al. | |
| 6,284,470 B1 | 9/2001 | Bitner et al. | |
| 6,296,937 B2 | 10/2001 | Pryor et al. | |
| 6,355,792 B1 * | 3/2002 | Michelsen ......... | C12N 15/1006 536/25.4 |
| 6,368,800 B1 | 4/2002 | Smith et al. | |
| 6,376,194 B2 | 4/2002 | Smith et al. | |
| 6,447,729 B1 | 9/2002 | Tuunanen | |
| 6,448,092 B1 | 9/2002 | Tuunanen | |
| 6,613,508 B1 | 9/2003 | Ness et al. | |
| 7,413,855 B2 | 8/2008 | Bergmann et al. | |
| 8,361,720 B2 | 1/2013 | Oldham-Haltom et al. | |
| 8,426,126 B2 | 4/2013 | Latham et al. | |
| 8,679,745 B2 | 3/2014 | Ballhause et al. | |
| 8,715,937 B2 | 5/2014 | Zou et al. | |
| 8,916,344 B2 | 12/2014 | Zou et al. | |
| 9,000,146 B2 | 4/2015 | Bruinsma et al. | |
| 9,212,392 B2 | 12/2015 | Allawi et al. | |
| 9,315,853 B2 | 4/2016 | Domanico et al. | |
| 9,394,332 B2 * | 7/2016 | Markert-Hahn ..... | C12Q 1/6806 |
| 10,030,272 B2 | 7/2018 | Ahlquist et al. | |
| 10,047,390 B2 | 8/2018 | Bruinsma et al. | |
| 10,144,953 B2 | 12/2018 | Domanico et al. | |
| 10,184,154 B2 | 1/2019 | Kisiel et al. | |
| 10,370,726 B2 | 8/2019 | Ahlquist et al. | |
| 10,465,248 B2 | 11/2019 | Allawi et al. | |
| 10,648,025 B2 | 5/2020 | Allawi et al. | |
| 10,704,081 B2 | 7/2020 | Lidgard et al. | |
| 10,822,638 B2 | 11/2020 | Allawi et al. | |
| 11,299,766 B2 | 4/2022 | Lidgard et al. | |
| 11,479,823 B2 | 10/2022 | Allawi et al. | |
| 2004/0219695 A1 | 11/2004 | Fox | |
| 2005/0089870 A1 | 4/2005 | Matsubara et al. | |
| 2005/0130172 A1 | 6/2005 | Beard et al. | |
| 2005/0208510 A1 | 9/2005 | Latham et al. | |
| 2006/0286577 A1 | 12/2006 | Jia | |
| 2007/0026435 A1 | 2/2007 | Templer | |
| 2007/0178466 A1 | 8/2007 | Hayatsu et al. | |

(Continued)

FOREIGN PATENT DOCUMENTS

| | | |
|---|---|---|
| CN | 109022417 | 12/2018 |
| EP | 1394172 | 3/2004 |

(Continued)

OTHER PUBLICATIONS

Sherbet et al. Isoelectric Characteristics and the Secondary Structure of Some Nucleic Acids. Biophys Struct Mech (1983) 10:121-128. (Year: 1983).*

Bailey et al., Single-tube analysis of DNA methylation with silica superparamagnetic beads. Clin Chem. Jun. 2010;56(6):1022-5.

Callinan et al., The emerging science of epigenomics. Hum Mol Genet. Apr. 15, 2006;15 Spec No. 1:R95-101.

CpGenome Universal Methylated DNA, Product Information, 2002-2009, Millipore, 3 pages.

Ehrich et al., A new method for accurate assessment of DNA quality after bisulfite treatment. Nucleic Acids Res. 2007;35(5):e29. 8 pages.

EL-Maarri. Methods: DNA methylation. Adv Exp Med Biol. 2003;544:197-204.

(Continued)

*Primary Examiner* — Yih-Horng Shiao

(74) *Attorney, Agent, or Firm* — Casimir Jones, S.C.; Mary Ann D. Brow

(57) ABSTRACT

The present disclosure provides methods and systems for purification of chemically modified, specifically, sulfonated DNA. Additionally, the disclosure provides methods and systems for bisulfite conversion with improved purification of sulfonated DNA using silica supports, such as silica beads, and acidic conditions for binding sulfonated DNA to silica surfaces.

16 Claims, 20 Drawing Sheets

(56) References Cited

U.S. PATENT DOCUMENTS

| | | | |
|---|---|---|---|
| 2007/0190530 | A1 | 8/2007 | Matsubara et al. |
| 2009/0042290 | A1 | 2/2009 | Steele et al. |
| 2009/0048439 | A1 | 2/2009 | Weisburg et al. |
| 2009/0093378 | A1 | 4/2009 | Bignell et al. |
| 2009/0263909 | A1 | 10/2009 | Millar et al. |
| 2010/0120033 | A1 | 5/2010 | Tomigahara et al. |
| 2011/0009277 | A1 | 1/2011 | Devos et al. |
| 2012/0122088 | A1 | 5/2012 | Zou et al. |
| 2012/0122106 | A1 | 5/2012 | Zou et al. |
| 2012/0262260 | A1 | 10/2012 | Light, II et al. |
| 2016/0010081 | A1 | 1/2016 | Allawi et al. |
| 2016/0090634 | A1 | 3/2016 | Kisiel et al. |
| 2016/0194721 | A1 | 7/2016 | Allawi et al. |
| 2017/0121704 | A1 | 5/2017 | Allawi et al. |
| 2017/0321286 | A1 | 11/2017 | Allawi et al. |
| 2019/0048399 | A1 | 2/2019 | Domanico et al. |
| 2022/0071605 | A1 | 3/2022 | Eisele et al. |
| 2022/0349009 | A1 | 11/2022 | Taylor et al. |

FOREIGN PATENT DOCUMENTS

| | | |
|---|---|---|
| JP | 2004089195 A | 3/2004 |
| WO | WO 1999/040098 | 8/1999 |
| WO | WO 2005/038051 | 4/2005 |
| WO | WO 2007/068437 | 6/2007 |
| WO | WO 2007/123553 | 11/2007 |
| WO | WO 2008/084219 | 7/2008 |
| WO | WO 2009/102788 | 8/2009 |
| WO | WO 2010/089538 | 8/2010 |
| WO | WO 2010/118016 | 10/2010 |
| WO | WO 2011/119934 | 9/2011 |
| WO | WO 2012/106525 | 8/2012 |
| WO | WO 2012/155072 | 11/2012 |
| WO | WO 2013/103889 | 7/2013 |
| WO | WO 2013/116375 | 8/2013 |
| WO | WO 2013/142545 | 9/2013 |
| WO | WO 2014/120918 | 8/2014 |
| WO | WO 2014/159650 | 10/2014 |
| WO | WO 2014/159652 | 10/2014 |
| WO | WO 2015/066695 | 5/2015 |
| WO | WO 2015/095689 | 6/2015 |
| WO | WO 2015/153283 | 10/2015 |
| WO | WO 2015/153284 | 10/2015 |
| WO | WO 2016/065295 | 4/2016 |
| WO | WO 2016/094813 | 6/2016 |
| WO | WO 2016/094839 | 6/2016 |
| WO | WO 2016/160454 | 10/2016 |
| WO | WO 2017/040627 | 3/2017 |
| WO | WO 2017/075061 | 5/2017 |
| WO | WO 2017/180886 | 10/2017 |
| WO | WO 2017/192221 | 11/2017 |
| WO | WO 2017/210372 | 12/2017 |
| WO | WO 2018/017710 | 1/2018 |
| WO | WO 2018/017740 | 1/2018 |
| WO | WO 2018/045322 | 3/2018 |
| WO | WO 2018/140781 | 8/2018 |
| WO | WO 2018/160576 | 9/2018 |
| WO | WO 2019/108626 | 6/2019 |
| WO | WO 2020/089691 | 5/2020 |
| WO | WO 2020/112869 | 6/2020 |
| WO | WO 2020/118274 | 6/2020 |
| WO | WO 2020/154665 | 7/2020 |
| WO | WO 2020/206256 | 10/2020 |
| WO | WO 2020/236939 | 11/2020 |
| WO | WO 2020/264220 | 12/2020 |
| WO | WO 2021/041726 | 3/2021 |
| WO | WO 2021/076969 | 4/2021 |
| WO | WO 2021/087275 | 5/2021 |
| WO | WO 2021/212031 | 10/2021 |
| WO | WO 2021/226071 | 11/2021 |
| WO | WO 2021/226074 | 11/2021 |
| WO | WO 2022/039904 | 2/2022 |
| WO | WO 2022/040306 | 2/2022 |
| WO | WO 2022/165247 | 8/2022 |
| WO | WO 2022/187227 | 9/2022 |
| WO | WO 2022/187695 | 9/2022 |
| WO | WO 2023/081796 | 5/2023 |
| WO | WO 2013/181651 | 12/2023 |

OTHER PUBLICATIONS

European Supplementary Search Report for EP13743659, mailed Aug. 4, 2015, 7 pages.
Fraga et al., DNA methylation: a profile of methods and applications. Biotechniques. Sep. 2002;33(3):632, 634, 636-49.
Frommer et al., A genomic sequencing protocol that yields a positive display of 5-methylcytosine residues in individual DNA strands. Proc Natl Acad Sci U S A. Mar. 1, 1992;89(5):1827-31.
Grigg et al., Sequencing 5-methylcytosine residues in genomic DNA. Bioessays. Jun. 1994; 16(6):431-6.
Grigg. Sequencing 5-methylcytosine residues by the bisulphite method. DNA Seq. 1996;6(4):189-98.
Grunau et al., Bisulfite genomic sequencing: systematic investigation of critical experimental parameters. Nucleic Acids Res. Jul. 1, 2001;29(13):E65-5.
Hayatsu et al., Bisulfite modification for analysis of DNA methylation. Curr Protoc Nucleic Acid Chem. Jun. 2008;Chapter 6:Unit 6.10. 15 pages.
Hayatsu et al., Progress in the bisulfite modification of nucleic acids. Nucleic Acids Symp Ser (Oxf). 2009;(53):217-8.
Hayatsu. Discovery of bisulfite-mediated cytosine conversion to uracil, the key reaction for DNA methylation analysis—a personal account. Proc Jpn Acad Ser B Phys Biol Sci. 2008;84(8):321-30.
Hayatsu. The bisulfite genomic sequencing used in the analysis of epigenetic states, a technique in the emerging environmental genotoxicology research. Mutat Res. Jul.-Aug. 2008;659(1-2):77-82.
Human Genomic DNA, Cat. No. 11 691 112 001, Product Information, Roche Diagnostics GmbH, 2013, 6 pages.
International Search Report and Written Opinion for PCT Application No. PCT/US2013/023908, mailed Apr. 12, 2013. 14 pages.
International Search Report and Written Opinion for PCT/US2021/043769. Mailed Mar. 15, 2022. 14 pages.
Katevatis et al., Low concentration DNA extraction and recovery using a silica solid phase. PLoS One. May 5, 2017;12(5):e0176848. 14 pages.
Laird et al., Hairpin-bisulfite PCR: assessing epigenetic methylation patterns on complementary strands of individual DNA molecules. Proc Natl Acad Sci U S A. Jan. 6, 2004;101(1):204-9.
Laird. The power and the promise of DNA methylation markers. Nat Rev Cancer. Apr. 2003;3(4):253-66.
Leontiou et al., Bisulfite Conversion of DNA: Performance Comparison of Different Kits and Methylation Quantitation of Epigenetic Biomarkers that Have the Potential to Be Used in Non-Invasive Prenatal Testing. PLoS One. Aug. 6, 2015;10(8):e0135058. 1-22.
Munson et al., Recovery of bisulfite-converted genomic sequences in the methylation-sensitive QPCR. Nucleic Acids Res. 2007;35(9):2893-903.
SiMAG—basic product information, chemicell, retrieved Nov. 7, 2013, 1 page.
Trust Microcon filters for DNA and protein samples, Product Brochure, EMD Milipore, 2012, 2 pages.
Zou et al., Quantification of methylated markers with a multiplex methylation-specific technology. Clin Chem. Feb. 2012;58(2):375-83.
Zymo Research, EZ DNA Methylation Kit, Instruction Manual, Ver. 1.2.5, zymoresearch.com/downloads/dl/file/id/56/d5001i.pdf, 17 pages, accessed Mar. 30, 2023.
Fujiwara et al., Adsorption of duplex DNA on mesoporous silicas: possibility of inclusion of DNA into their mesopores. Anal Chem. Dec. 15, 2005;77(24):8138-45.
Melzak et al., Driving Forces for DNA Adsorption to Silica in Perchlorate Solutions. Journal of Colloid and Interface Science. Aug. 10, 1996;191(2):635-644.
Extended EP Search Report for EP21858796.2, mailed Jun. 17, 2024, 22 pages.

* cited by examiner

FIG. 8A

| | | | | LASS4-S Strands | | LRRC4-AS Strands | | SDC2-S Strands | | PPP2R5C-S Strands | | ZDHHC1-AS Strands | | |
|---|---|---|---|---|---|---|---|---|---|---|---|---|---|---|
| BND SLN | ABS Lot | DOM | ABS pH | Median | CV | Median | CV | Median | CV | Median | CV | Median | CV | N |
| Non-adjusted | 2278 | 31-Oct-10 | 4.74 | 1294 | 7 | 1711 | 8 | 4878 | 7 | 5111 | 74 | 9819 | 7 | 5 |
| | 5600010116 | 31-Jan-18 | 5.37 | 1250 | 5 | 1738 | 5 | 2443 | 12 | 394 | 6 | 6663 | 14 | 6 |
| | 5600010134 | 30-Apr-18 | 5.37 | 1217 | 9 | 1731 | 8 | 2192 | 6 | 359 | 10 | 5752 | 7 | 6 |
| | 5600010173 | 31-Oct-18 | 5.37 | 1271 | 12 | 1736 | 7 | 1488 | 10 | 276 | 16 | 4640 | 9 | 6 |
| pH ~3 | 2278 | 31-Oct-10 | 4.74 | 1137 | 5 | 1571 | 8 | 4643 | 8 | 14171 | 17 | 8376 | 6 | 5 |
| | 5600010116 | 31-Jan-18 | 5.37 | 1264 | 9 | 1751 | 5 | 4851 | 8 | 15320 | 9 | 9726 | 9 | 5 |
| | 5600010134 | 30-Apr-18 | 5.37 | 1290 | 7 | 1721 | 7 | 5069 | 5 | 15993 | 6 | 9592 | 11 | 6 |
| | 5600010173 | 31-Oct-18 | 5.37 | 1301 | 6 | 1681 | 7 | 4927 | 7 | 15113 | 6 | 9387 | 7 | 6 |

FIG. 8B

| | | Strands_LASS4 | | | Strands_LRRC4 | | | Strands_ZDHHC1 | | | Strands_PPP2R5C | | | Strands_ZDHHC1 | | | |
|---|---|---|---|---|---|---|---|---|---|---|---|---|---|---|---|---|---|
| BND Cond. | % ABS Stock | Median | % Diff | CV | Median | % Diff | CV | Median | % Diff | CV | Median | % Diff | CV | Median | % Diff | CV | N |
| No Adjustment | 56.6 | 1224 | NA | 11 | 4538 | NA | 8 | 4547 | NA | 9 | 2784 | NA | 9 | 5275 | NA | 8 | 8 |
| | 50 | 1346 | 10 | 9 | 4453 | -2 | 6 | 6110 | 34 | 8 | 3229 | 16 | 7 | 7243 | 37 | 10 | 8 |
| | 43 | 1409 | 15 | 7 | 3845 | -15 | 3 | 6786 | 49 | 10 | 3069 | 10 | 11 | 8371 | 59 | 7 | 7 |
| Citric Acid Buffer | 56.6 | 1167 | NA | 8 | 4058 | NA | 6 | 5675 | NA | 9 | 2843 | NA | 10 | 6759 | NA | 9 | 8 |
| | 50 | 1272 | 9 | 9 | 4115 | 1 | 6 | 6169 | 9 | 10 | 3080 | 8 | 9 | 7014 | 4 | 11 | 8 |
| | 43 | 1277 | 9 | 8 | 3576 | -12 | 8 | 6162 | 9 | 12 | 2885 | 1 | 8 | 7110 | 5 | 8 | 7 |

FIG. 9

| Marker | BND pH | ABS Cond | BND SLN | Strands Mean | Strands CV | % Diff C-N | N |
|---|---|---|---|---|---|---|---|
| LASS4_4482 | Non-Adjusted | 57% | Nominal | 1622 | 5 | | 11 |
| | | | Contaminated | 1569 | 3 | -3 | 10 |
| | Low | 50% | Nominal | 1670 | 7 | | 11 |
| | | | Contaminated | 1635 | 6 | -2 | 11 |
| LRRC4 | Non-Adjusted | 57% | Nominal | 3534 | 4 | | 11 |
| | | | Contaminated | 3405 | 4 | -4 | 10 |
| | Low | 50% | Nominal | 3107 | 9 | | 11 |
| | | | Contaminated | 3092 | 6 | 0 | 11 |
| PPP2R5C | Non-Adjusted | 57% | Nominal | 53495 | 4 | | 11 |
| | | | Contaminated | 43960 | 10 | -18 | 10 |
| | Low | 50% | Nominal | 54868 | 5 | | 11 |
| | | | Contaminated | 56908 | 7 | 4 | 11 |
| ZDHHC1 | Non-Adjusted | 57% | Nominal | 4567 | 13 | | 11 |
| | | | Contaminated | 2478 | 11 | -46 | 10 |
| | Low | 50% | Nominal | 5522 | 6 | | 11 |
| | | | Contaminated | 5233 | 12 | -5 | 11 |
| | Non-Adjusted | 57% | Nominal | 4256 | 8 | | 11 |
| | | | Contaminated | 2726 | 8 | -36 | 10 |
| | Low | 50% | Nominal | 5159 | 9 | | 11 |
| | | | Contaminated | 5549 | 9 | 8 | 11 |

FIG. 10

| Binding Bead | FAM NDRG4 | | HEX BMP3 | | Quasar BTACT | | N per Channel |
|---|---|---|---|---|---|---|---|
| | Log Strands | | Log Strands | | Log Strands | | |
| | Average | Ctrl Delta | Average | Ctrl Delta | Average | Ctrl Delta | |
| Control | 3.48 | | 3.01 | | 4.70 | | 16 |
| Bead B | 0.0 | -3.48 | 0.00 | -3.01 | 0.00 | -4.70 | 16 |
| Bead F | 0.0 | -3.48 | 0.00 | -3.01 | 0.00 | -4.70 | 14 |
| Control | 3.39 | | 3.06 | | 4.59 | | 22 |
| Bead G | 3.29 | -0.11 | 2.95 | -0.11 | 4.46 | -0.13 | 24 |
| Control | 3.90 | | 3.53 | | 5.15 | | 76 |
| Bead E | 3.91 | 0.01 | 3.50 | -0.02 | 4.96 | -0.20 | 16 |
| Control | 3.139 | | 3.025 | | 4.573 | | 22 |
| Bead C | 3.110 | -0.03 | 2.965 | -0.06 | 4.496 | -0.08 | 22 |
| Control | 2.739 | | 2.054 | | 3.789 | | |
| Bead A | 2.761 | 0.02 | 2.042 | -0.01 | 3.658 | -0.13 | |

FIG. 11

| Binding Bead | Log Strands LASS4 | | Log Strands LRRC4 | | Log Strands SDC2 | | Log Strands PPP2R5C | | Log Strands ZDHHC1 | | N |
|---|---|---|---|---|---|---|---|---|---|---|---|
| | Median | Ctrl Difference | Median | Ctrl Difference | Median | Ctrl Difference | Median | Ctrl Difference | Median | Ctrl Difference | |
| Control | 3.14 | NA | 3.21 | NA | 3.65 | NA | 4.01 | NA | 3.80 | NA | 6 |
| Bead A | 3.09 | -0.05 | 3.20 | -0.01 | 3.64 | -0.01 | 4.06 | 0.05 | 3.79 | -0.01 | 6 |
| Bead B | 3.23 | 0.09 | 3.06 | -0.15 | 3.27 | -0.38 | 3.07 | -0.93 | 3.28 | -0.52 | 6 |
| Bead C | 3.10 | -0.04 | 3.20 | -0.01 | 3.58 | -0.07 | 3.64 | -0.36 | 3.78 | -0.02 | 6 |
| Bead D | 3.94 | 0.80 | 3.10 | -0.11 | 3.81 | 0.16 | 4.31 | 0.30 | 3.44 | -0.36 | 6 |
| Bead E | 3.09 | -0.05 | 3.20 | -0.01 | 3.65 | 0.00 | 4.07 | 0.06 | 3.80 | -0.01 | 6 |
| Bead F | 3.45 | 0.31 | 3.17 | -0.04 | 3.55 | -0.10 | 3.57 | -0.44 | 3.35 | -0.46 | 5 |
| Bead G | 3.14 | 0.00 | 3.20 | -0.01 | 3.45 | -0.20 | 3.00 | -1.01 | 3.73 | -0.07 | 5 |

FIG. 12

| | Strands_LASS4 | | Strands_LRRC4 | | Strands_SDC2 | | Strands_PPP2R5C | | Strands_ZDHHC1 | | |
|---|---|---|---|---|---|---|---|---|---|---|---|
| BND pH | Median | CV | Median | CV | Median | CV | Median | CV | Median | CV | N |
| 4.85 | 1010 | 9 | 2366 | 11 | 2024 | 13 | 551 | 17 | 3995 | 10 | 8 |
| 3.87 | 980 | 5 | 2155 | 6 | 4491 | 7 | 18167 | 8 | 7478 | 7 | 8 |
| 2.94 | 970 | 6 | 2236 | 7 | 4523 | 7 | 19119 | 9 | 6970 | 7 | 8 |
| 2.79 | 963 | 4 | 2146 | 6 | 4155 | 7 | 18468 | 8 | 6823 | 7 | 8 |
| 2.51 | 922 | 4 | 2161 | 7 | 4148 | 8 | 18820 | 9 | 6373 | 6 | 7 |
| 2.13 | 914 | 5 | 2035 | 4 | 4002 | 5 | 16316 | 9 | 6087 | 6 | 7 |

FIG. 13

| | | | Strands_LASS4 | | | Strands_PPP2R5C | | | Strands_LRRC4 | | | Strands_ZDHHC1 | | | |
|---|---|---|---|---|---|---|---|---|---|---|---|---|---|---|---|
| [DNA] ng/rxn | DNA Size (bp) | BST Chemistry | Median | %Diff Chemistry | CV | Median | %Diff Chemistry | CV | Median | %Diff Chemistry | CV | Median | %Diff Chemistry | CV | N |
| 300 | 200 | Non-Adjusted pH | 22997 | 4 | 6 | 18248 | 1 | 9 | 16362 | -1 | 7 | 17501 | 23 | 10 | 6 |
| | | Low pH | 23845 | | 10 | 18399 | | 6 | 16184 | | 6 | 21561 | | 9 | 6 |
| | 3600 | Non-Adjusted pH | 22770 | 3 | 8 | 17564 | 5 | 9 | 17356 | -6 | 9 | 20366 | 14 | 20 | 6 |
| | | Low pH | 23354 | | 7 | 18470 | | 6 | 16390 | | 9 | 23205 | | 8 | 6 |
| | 20000 | Non-Adjusted pH | 22446 | 1 | 9 | 18590 | 0 | 7 | 17821 | -9 | 18 | 22591 | 6 | 19 | 6 |
| | | Low pH | 22559 | | 6 | 18598 | | 9 | 16144 | | 14 | 23839 | | 9 | 6 |
| 2700 | 200 | Non-Adjusted pH | 23949 | 10 | 7 | 13889 | 33 | 16 | 19566 | -8 | 14 | 11369 | 132 | 20 | 6 |
| | | Low pH | 26328 | | 7 | 18530 | | 11 | 17925 | | 13 | 26383 | | 10 | 6 |
| | 3600 | Non-Adjusted pH | 23897 | 9 | 8 | 15967 | 18 | 11 | 20561 | -11 | 15 | 12909 | 114 | 25 | 6 |
| | | Low pH | 26126 | | 9 | 18779 | | 9 | 18351 | | 11 | 27644 | | 10 | 6 |
| | 20000 | Non-Adjusted pH | 23474 | 6 | 4 | 17913 | 10 | 11 | 19850 | -6 | 9 | 17312 | 76 | 5 | 6 |
| | | Low pH | 24897 | | 7 | 19707 | | 4 | 18658 | | 9 | 30533 | | 8 | 6 |
| 5400 | 200 | Non-Adjusted pH | 18431 | 36 | 7 | 7240 | 118 | 37 | 14427 | 22 | 8 | 4547 | 374 | 25 | 6 |
| | | Low pH | 25066 | | 12 | 15768 | | 9 | 17611 | | 7 | 21535 | | 4 | 6 |
| | 3600 | Non-Adjusted pH | 17965 | 35 | 8 | 8037 | 105 | 33 | 15166 | 18 | 9 | 5461 | 351 | 27 | 6 |
| | | Low pH | 24284 | | 7 | 16448 | | 9 | 17946 | | 5 | 24641 | | 5 | 6 |
| | 20000 | Non-Adjusted pH | 21441 | 11 | 5 | 12797 | 37 | 13 | 19266 | -5 | 6 | 13472 | 138 | 18 | 6 |
| | | Low pH | 23710 | | 8 | 17552 | | 5 | 18350 | | 5 | 32042 | | 6 | 6 |

FIG. 14

| Step | Reaction Config. | Protocol 1 | | Protocol 2 | | Reaction Config. | Protocol 3 | |
|---|---|---|---|---|---|---|---|---|
| | | Reagents [rxn] | Incubation Parameters | Reagents [rxn] | Incubation Parameters | | Reagents [rxn] | Incubation Parameters |
| **Denaturation** | 80 µL after transfer | 89mM NaOH, 10 ng/µL BSA | 20 min @ 42°C | **80mM NaOH, 18 ng/µL BSA** | **3 min @ 32.5°C mix** | 75 µL Sample + 9 µL NaOH + 11 µL CAR SLN = **95 µL** | **94mM NaOH, 10.4 ng/µL BSA** | 1 min mix |
| **Bisulfite** | 80 µL + 120 µL ABS = 200 µL | 34% ABS | 75 min @ 65.5°C | **31% ABS** | **88 min @ 62.5°C** | 95 µL + 120 µL ABS = 215 µL | **29% ABS** | 75 min @ 65.5°C |
| **DNA Binding** | 200 µL + 750 µL BND SLN + 50 µL BND BDS = 1 mL | 5.25M GuHCl, 0.8 mg/mL Silica Beads | 30 min @ 30.5°C mix | 5.25M GuHCl, **100mM Citrate, pH 3.7,** 0.8 mg/mL Silica Beads | **15 min @ 32.5°C mix** | 215 µL + 750 µL BND SLN + 50 µL BND BDS = 1015 µL | 5.17M GuHCl, 0.79 mg/mL Silica Beads | 30 min @ 30.5°C mix |
| **2X Alcohol Wash** | Wash1 = 1 mL Wash2 = 250 µL | 80% EtOH, 10mM Tris, pH 8.0 | 3 min mix | **75% IPA, 20mM Tris, pH 7.8** | 3 min mix | Wash1 = 1 mL Wash2 = 250 µL | 80% EtOH, 10mM Tris, pH 8.0 | 3 min mix |
| **Desulfonation** | 200 µL | 105mM NaOH, 70% IPA | 7 min @ 30.5°C mix | **30mM NaOH,** 70% IPA | **3 min @ 32.5°C mix** | 200 µL | **87.5mM NaOH, 75% IPA** | 7 min @ 30.5°C mix |
| **2X Alcohol Wash** | 250 µL | 80% EtOH, 10mM Tris, pH 8.0 | 3 min mix | **75% IPA, 20mM Tris, pH 7.8** | 3 min mix | 250 µL | 80% EtOH, 10mM Tris, pH 8.0 | 3 min mix |
| **Drying** | Beads Only | N/A | 15 min @ 71.5°C mix | N/A | 15 min @ 71.5°C mix | Beads Only | N/A | 15 min @ 71.5°C mix |
| **Elution** | 70 µL | 10mM Tris, pH 8.0, 0.1mM EDTA | 25 min @ 66.5°C mix, 8 min cool | **3mM Tris, pH 7.8,** 0.1mM EDTA | 25 min @ 66.5°C mix, **25 min cool** | 80 µL | **4mM Tris,** pH 8.0, 0.1mM EDTA | 25 min @ **66.5°C mix,** 20 min cool |

FIG. 15A

| DNA Concentration (ng/μL) | ZNF568 Protocol 1 | ZNF568 Protocol 3 | ZNF568 Protocol 2 | BMP3 Protocol 1 | BMP3 Protocol 3 | BMP3 Protocol 2 | B3GALT6 Protocol 1 | B3GALT6 Protocol 3 | B3GALT6 Protocol 2 |
|---|---|---|---|---|---|---|---|---|---|
| 26.7 | 39,626 | 71,018 | 48,450 | 43,079 | 72,235 | 50,490 | 34,338 | 51,796 | 37,904 |
| | 56,602 | 32,350 | 40,639 | 61,384 | 31,153 | 44,642 | 43,878 | 25,573 | 32,888 |
| | 41,582 | 28,539 | 42,777 | 43,943 | 29,736 | 46,500 | 30,895 | 25,509 | 34,818 |
| | 43,044 | 37,082 | 48,245 | 46,255 | 38,629 | 52,040 | 34,662 | 29,768 | 40,594 |
| 17.8 | 32,248 | 35,915 | 47,662 | 34,498 | 39,031 | 54,563 | 29,143 | 31,895 | 45,336 |
| | 53,938 | 15,347 | 33,690 | 63,749 | 15,051 | 38,963 | 49,199 | 13,677 | 31,703 |
| | 25,725 | 28,515 | 40,330 | 28,208 | 29,235 | 47,893 | 23,727 | 25,594 | 38,256 |
| | 36,763 | 31,608 | 40,455 | 41,355 | 33,161 | 46,938 | 33,535 | 28,455 | 37,481 |
| 11.87 | 19,156 | 33,522 | 34,265 | 22,045 | 36,571 | 42,594 | 18,444 | 30,656 | 33,161 |
| | 28,941 | 17,138 | 22,290 | 33,582 | 18,274 | 28,252 | 28,112 | 15,989 | 22,800 |
| | 22,520 | 13,659 | 48,385 | 26,234 | 14,060 | 56,816 | 22,114 | 12,514 | 45,903 |
| | 37,025 | 16,420 | 45,946 | 43,599 | 17,467 | 57,314 | 34,477 | 15,205 | 44,608 |
| 7.91 | 13,998 | 23,168 | 17,087 | 15,528 | 27,367 | 21,598 | 13,806 | 22,619 | 16,480 |
| | 19,546 | 9,023 | 15,566 | 24,312 | 9,837 | 19,206 | 19,722 | 8,913 | 14,702 |
| | 16,848 | 9,686 | 35,074 | 19,306 | 10,965 | 44,319 | 16,141 | 9,284 | 34,327 |
| | 19,108 | 19,899 | 30,456 | 23,996 | 24,318 | 36,382 | 18,995 | 18,732 | 27,818 |
| 5.27 | 10,208 | 11,458 | 17,292 | 12,249 | 13,008 | 22,539 | 10,322 | 11,771 | 16,705 |
| | 11,543 | 5,666 | 12,572 | 14,894 | 6,223 | 16,820 | 12,419 | 5,787 | 13,143 |
| | 10,895 | 8,245 | 10,728 | 13,390 | 8,975 | 14,668 | 11,050 | 8,122 | 10,295 |
| | 12,132 | 11,157 | 10,595 | 14,775 | 13,350 | 14,181 | 12,153 | 11,251 | 10,107 |
| 3.52 | 5,493 | 8,189 | 6,193 | 6,378 | 9,532 | 8,313 | 5,666 | 8,156 | 6,473 |
| | 6,483 | 4,635 | 6,008 | 7,627 | 4,669 | 8,175 | 7,033 | 4,755 | 6,112 |
| | 7,550 | 6,583 | 7,017 | 8,553 | 7,281 | 9,411 | 7,550 | 6,718 | 6,758 |
| | 8,166 | 8,414 | 6,536 | 9,591 | 9,684 | 8,850 | 7,983 | 8,124 | 6,282 |

FIG. 15B

| DNA Concentration (ng/µL) | NDRG4 Protocol 1 | NDRG4 Protocol 3 | NDRG4 Protocol 2 | VAV3 Protocol 1 | VAV3 Protocol 3 | VAV3 Protocol 2 | ZNF682 Protocol 1 | ZNF682 Protocol 3 | ZNF682 Protocol 2 |
|---|---|---|---|---|---|---|---|---|---|
| 26.7 | 54,579 | 71,401 | 84,365 | 7,763 | 4,241 | 9,267 | 23,879 | 36,389 | 44,687 |
| | 74,463 | 113,450 | 96,567 | 10,761 | 7,981 | 11,048 | 33,525 | 58,351 | 51,426 |
| | 82,988 | 87,382 | 91,486 | 12,601 | 6,305 | 11,373 | 39,963 | 41,870 | 49,000 |
| | 65,865 | 103,912 | 103,795 | 9,450 | 8,234 | 13,014 | 28,852 | 52,389 | 58,478 |
| 17.8 | 45,640 | 41,100 | 66,471 | 7,007 | 2,793 | 8,193 | 21,341 | 22,056 | 36,258 |
| | 83,030 | 63,222 | 74,197 | 12,708 | 4,974 | 9,131 | 41,076 | 32,005 | 40,385 |
| | 63,791 | 90,962 | 79,613 | 9,711 | 6,380 | 10,931 | 28,248 | 45,886 | 46,723 |
| | 50,725 | 85,837 | 81,241 | 8,132 | 6,824 | 11,271 | 23,668 | 44,426 | 46,846 |
| 11.87 | 34,977 | 39,872 | 41,211 | 5,423 | 3,092 | 5,210 | 16,034 | 22,526 | 23,643 |
| | 49,292 | 64,382 | 41,126 | 9,046 | 5,772 | 5,684 | 25,562 | 36,649 | 23,967 |
| | 54,883 | 32,217 | 57,932 | 9,851 | 2,601 | 8,679 | 27,027 | 16,778 | 34,467 |
| | 49,077 | 38,279 | 62,665 | 8,596 | 3,489 | 9,115 | 23,621 | 20,947 | 38,354 |
| 7.91 | 24,897 | 26,435 | 28,998 | 4,434 | 2,337 | 3,598 | 13,115 | 17,499 | 16,340 |
| | 40,522 | 40,971 | 29,016 | 7,804 | 3,798 | 3,958 | 22,691 | 25,529 | 18,359 |
| | 36,154 | 36,757 | 35,206 | 6,398 | 3,344 | 5,369 | 19,488 | 21,577 | 22,049 |
| | 24,530 | 39,001 | 31,904 | 4,737 | 4,029 | 4,720 | 13,923 | 22,328 | 20,384 |
| 5.27 | 19,926 | 16,987 | 18,182 | 3,975 | 1,463 | 2,395 | 11,302 | 10,661 | 11,007 |
| | 35,761 | 18,291 | 21,551 | 7,560 | 2,158 | 3,096 | 21,628 | 12,226 | 13,944 |
| | 20,371 | 25,714 | 20,705 | 4,320 | 2,753 | 2,909 | 12,725 | 16,002 | 13,540 |
| | 17,815 | 18,417 | 21,115 | 3,668 | 2,154 | 3,149 | 10,768 | 11,647 | 14,569 |
| 3.52 | 12,505 | 11,598 | 12,458 | 2,641 | 1,276 | 1,777 | 7,944 | 8,399 | 8,434 |
| | 17,011 | 18,760 | 12,803 | 3,799 | 2,213 | 1,987 | 10,974 | 13,331 | 9,013 |
| | 11,844 | 18,533 | 14,125 | 2,698 | 2,037 | 2,075 | 8,366 | 12,423 | 9,619 |
| | 8,860 | 12,245 | 13,889 | 2,161 | 1,438 | 2,150 | 5,849 | 8,400 | 9,601 |

FIG. 16

| DNA Conc. (ng/uL) | Protocol 2/ Protocol 1 or 3 | B3GALT6 | BMP3 | NDRG4 | VAV3 | ZNF568 | ZNG682 |
|---|---|---|---|---|---|---|---|
| 3.52 | Protocols 2:1 | 91% | 108% | 106% | 71% | 93% | 111% |
| 3.52 | Protocols 2:3 | 92% | 112% | 87% | 115% | 93% | 86% |
| 5.27 | Protocols 2:1 | 109% | 123% | 87% | 59% | 114% | 94% |
| 5.27 | Protocols 2:3 | 136% | 164% | 103% | 135% | 140% | 105% |
| 7.91 | Protocols 2:1 | 136% | 146% | 99% | 75% | 141% | 111% |
| 7.91 | Protocols 2:3 | 157% | 168% | 87% | 131% | 159% | 89% |
| 11.87 | Protocols 2:1 | 142% | 147% | 108% | 87% | 140% | 131% |
| 11.87 | Protocols 2:3 | 197% | 214% | 116% | 192% | 187% | 124% |
| 17.8 | Protocols 2:1 | 113% | 112% | 124% | 105% | 109% | 149% |
| 17.8 | Protocols 2:3 | 153% | 162% | 107% | 188% | 146% | 118% |
| 26.7 | Protocols 2:1 | 102% | 99% | 135% | 110% | 100% | 161% |
| 26.7 | Protocols 2:3 | 110% | 113% | 100% | 167% | 107% | 108% |

FIG 18

| | | | | Strands LASS4 | | Strands LRRC4 | | Strands PPP2R5C | | Strands ZDHHC1 | | |
|---|---|---|---|---|---|---|---|---|---|---|---|---|
| Added Buffer | pKa/ pK1 | pH Buffer Range | mM Rxn | Median | CV | Median | CV | Median | CV | Median | CV | N |
| None | NA | NA | NA | 998 | 6 | 2139 | 5 | 1818 | 16 | 4341 | 11 | 10 |
| Glycine | 2.35 | 2.2-3.6 | 126 | 942 | 10 | 2035 | 7 | 16819 | 8 | 5875 | 10 | 9 |
| Citrate | 4.76 | 3.0-6.2 | 85 | 953 | 9 | 1959 | 7 | 10712 | 6 | 5369 | 12 | 9 |
| Malate | 3.4 | 2.7-4.2 | 128 | 945 | 7 | 1949 | 9 | 8958 | 10 | 4977 | 17 | 9 |
| Formate | 3.75 | 3.0-4.5 | 203 | 978 | 7 | 1984 | 9 | 2856 | 9 | 4575 | 17 | 9 |

PURIFICATION OF SULFONATED DNA

The present application claims priority to U.S. Provisional Application Ser. No. 63/058,179, filed Jul. 29, 2020, which is incorporated herein by reference.

FIELD OF THE INVENTION

The present disclosure relates to the purification of sulfonated DNA. Additionally, the disclosure is related to methods and systems for bisulfite conversion of DNA and improved purification of sulfonated DNA with supports, e.g., silica supports, and use of acidic conditions for binding sulfonated DNA to supports.

BACKGROUND OF THE INVENTION

DNA methylation is an epigenetic mechanism that occurs by the addition of a methyl group to DNA, specifically the cytosine ring of DNA, thereby modifying the function of the gene. Detecting and mapping sites of DNA methylation are essential for understanding epigenetic gene regulation and detecting aberrant DNA methylation involved in the development and progression of cancer and other disease states.

Mapping methylation sites is currently accomplished by the bisulfite method described by Frommer, et al. for the detection of 5-methylcytosines in DNA (*Proc. Natl. Acad. Sci. USA* 89: 1827-31 (1992), incorporated herein by reference in its entirety for all purposes) or variations thereof. The bisulfite method of mapping 5-methylcytosines is based on the observation that cytosine, but not 5-methylcytosine, reacts with bisulfite. Usually, the reaction includes a series of steps, including: reacting cytosine with hydrogen sulfite to form sulfonated cytosine; spontaneous deamination of the sulfonated reaction intermediate which results in sulfonated uracil; and desulfonating uracil under alkaline conditions to form uracil. Base pair differences between uracil and 5-methylcytosine facilitate detection—uracil base pairs with adenine and 5-methylcytosine base pairs with guanine. Thus, a variety of methods are able to differentiate methylated cytosines from non-methylated cytosines, e.g., bisulfite genomic sequencing (Grigg G, & Clark S, *Bioessays* (1994) 16: 431-36; Grigg G, *DNA Seq.* (1996) 6: 189-98) or methylation-specific PCR (MSP) as is disclosed, e.g., in U.S. Pat. No. 5,786,146. A large number of variations in reaction conditions, concentrations of reagents, and the like are known in the art for bisulfite conversions and each variation may lead to differences in DNA recovery rates and levels of deamination.

In general, bisulfite treatment methods include washing steps and buffer changes to produce a purified, converted DNA sample for base pair analysis. A variety of approaches facilitate these steps, e.g., spin columns, ethanol purification, and solid supports. However, methods using silica spin columns or ethanol purification often result in sample losses that compromise the usefulness of the bisulfite method as a measure of cytosine methylation. Though some improvements have been developed using solid supports, these methods require large amounts of DNA as input and also suffer from problems of sample loss and reproducibility. Additionally, conventional methods often require days-long times to complete and do not provide an efficient conversion and recovery of the converted DNA. Consequently, conventional methods provide only qualitative measures of DNA methylation.

In trying to optimize the bisulfite conversion of DNA, the focus has generally been on the bisulfite modification reaction itself, i.e., the step of sulfonating unmethylated cytosines in the DNA. Some methods of improving recovery of the resulting sulfonated DNA have focused on increasing chaotropic salt concentration thereby disrupting the hydrogen bond of water with DNA to promote silica-DNA interaction. Other methods have addressed the decreased recovery of cytosine-rich DNA by simplifying the binding buffer, where additives such as alcohol and TRIS are removed, e.g., in U.S. Pat. No. 9,315,853, incorporated herein by reference in its entirety for all purposes.

SUMMARY

The systems and methods disclosed herein increase bisulfite converted DNA recovery, especially for cytosine-rich targets, improve robustness to variations in the bisulfite treatment process, and increase DNA recovery for a wide range of sample types. The methods include neutralizing DNA charge to promote silica-DNA interaction in addition to hydrogen bond disruption.

Disclosed herein are methods comprising binding sulfonated DNA to silica supports in an acidic solution, wherein the acidic solution has a pH less than or equal to an isoelectric point pH(I) of the sulfonated DNA. In some embodiments, the pH is less than 5. In some embodiments, the pH is between 2.5 and 4. The acidic solution may further comprise a chaotropic salt or agent. In some embodiments, the chaotropic salt is guanidine hydrochloride (GuHCl).

The methods may further comprise incubating denatured, non-sulfonated DNA with a sulfonation reagent to produce the sulfonated DNA. As used herein, the term "sulfonation reagent" preferably refers to a reagent that selectively converts unmethylated cytosine nucleotides to uracil sulfonate nucleotides. In some embodiments, the sulfonation reagent is ammonium bisulfite.

The methods may further comprise at least one or all of: washing silica supports bound to sulfonated DNA; desulfonating the sulfonated DNA to form desulfonated DNA; and eluting the desulfonated DNA from the silica supports. In some embodiments, the washing is done with an alcohol, e.g., ethanol. In some embodiments, the desulfonating comprises incubation of sulfonated DNA at alkaline conditions and in some embodiments, sulfonated DNA is added directly to a detection assay, e.g., a polymerase chain reaction, such that the sulfonated DNA is desulfonated under the conditions of the conducting the detection assay. In some embodiments, the elution comprises treatment with high heat.

The technology further encompasses and is illustrated by the following embodiments:

1. A method comprising combining sulfonated DNA and a silica support in an acidic binding solution, wherein the acidic binding solution has a pH less than or equal to an isoelectric point (pH(I)) of the sulfonated DNA, and wherein sulfonated DNA is bound to the silica support.
2. The method of embodiment 1, wherein the silica support comprises at least one of a particle, a bead, and a fiber.
3. The method of embodiment 1, wherein the silica support is magnetic.
4. The method of embodiment 1, wherein the pH of the acidic binding solution is less than 5.
5. The method of embodiment 4, wherein the pH of the acidic binding solution is between 2.0 and 4.
6. The method of embodiment 1, wherein the acidic binding solution comprises a chaotropic salt.

7. The method of embodiment 6, wherein the chaotropic salt comprises at least one of guanidine hydrochloride (GuHCl) and guanidine isothiocyanate (GITC).
8. The method of embodiment 1, the method further comprises incubating single-stranded non-sulfonated DNA or partially-sulfonated DNA with a sulfonation reagent to produce the sulfonated DNA.
9. The method of embodiment 8, wherein the sulfonation reagent comprises at least one of ammonium bisulfite and sodium bisulfite.
10. The method of embodiment 1, further comprising at least one of:
    i) washing a silica support bound to sulfonated DNA;
    ii) desulfonating the sulfonated DNA to form desulfonated DNA; and
    iii) eluting the desulfonated DNA from the silica support.
11. The method of embodiment 8, wherein incubating non-sulfonated DNA with a sulfonation reagent is in a sulfonation reaction solution having a pH at or above the pH(I) of the sulfonated DNA.
12. The method of embodiment 11, wherein at least a portion of the sulfonation reaction solution is removed from the sulfonated DNA prior to the combining of the sulfonated DNA and the silica support in the acidic binding solution.
13. The method of embodiment 12, wherein essentially all of the sulfonation reaction solution is removed from the sulfonated DNA prior to combining the sulfonated DNA and the silica support in the acidic binding solution.
14. The method of embodiment 12, wherein at least a portion of the sulfonation reaction solution is removed from the sulfonated DNA by size exclusion filtration.
15. The method of embodiment 11, wherein the acidic binding solution is formed by adding an acidic component to the sulfonated DNA in the sulfonation reaction solution.
16. The method of embodiment 15, wherein the acidic component is an acidic solution.
17. The method of embodiment 16, wherein the acidic component comprises at least one of an acidic acetate, glycine, malate, formate, or citrate solution.
18. The method of embodiment 15, wherein the acidic component comprises a chaotropic salt.
19. The method of embodiment 18, wherein the chaotropic salt comprises at least one of GuHCl and GITC.
20. A method of preparing desulfonated DNA, comprising:
    i) incubating single-stranded non-sulfonated DNA or partially-sulfonated DNA with a sulfonation reagent to produce sulfonated DNA in a sulfonation reaction mixture;
    ii) combining the sulfonation reaction mixture with:
        a) an acidic component; and
        b) chaotropic salt; and
        c) a silica support
    to form an acidic binding solution, wherein the acidic binding solution has a pH less than or equal to an isoelectric point (pH(I)) of the sulfonated DNA, and wherein sulfonated DNA is bound to the silica support;
    iii) separating sulfonated DNA bound to the silica support from the acidic binding solution;
    iv) treating separated sulfonated DNA under conditions wherein the sulfonated DNA is desulfonated.
21. The method of embodiment 20, wherein the non-sulfonated DNA comprises one or more unmethylated cytosine nucleotides, and wherein the desulfonated DNA comprises one or more deoxyuracil nucleotides.
22. The method of embodiment 20, wherein treating separated sulfonated DNA under conditions wherein the sulfonated DNA is desulfonated comprises combining sulfonated DNA with a desulfonation solution.
23. The method of embodiment 22, wherein the desulfonation solution is combined with sulfonated DNA that is bound to the silica support.
24. A composition comprising sulfonated DNA and a silica support in an acidic binding solution comprising a chaotropic salt, wherein the acidic binding solution has a pH less than or equal to a pH(I) of the sulfonated DNA, and wherein the sulfonated DNA is bound to the silica support.
25. The composition of embodiment 24, wherein the chaotropic salt comprises at least one of GuHCl and GITC.
26. The composition of embodiment 24, wherein the acidic binding solution comprises at least one of a acetate, glycine, malate, formate, or citrate buffer.
27. The composition of embodiment 26, wherein the acidic binding solution comprises a citrate buffer.
28. The composition of embodiment 24, wherein the acidic binding solution comprises a bisulfite salt.
29. The composition of embodiment 28, wherein the bisulfite salt is ammonium bisulfite.
30. The composition of embodiment 24, wherein the pH of the acidic binding solution is less than 5.
31. The composition of embodiment 30, wherein the pH of the acidic binding solution is between 2.0 and 4.
32. A kit, comprising:
    i) a bisulfite reagent solution or components for preparing a bisulfite reagent solution;
    ii) a silica support; and
    iii) an acidic component having a pH less than or equal to a pH(I) of sulfonated DNA.
33. The kit of embodiment 32, wherein the bisulfite reagent solution has a pH that is greater than the pH(I) of sulfonated DNA.
34. The kit of embodiment 32, wherein the acidic component is an acidic solution.
35. The kit of embodiment 33, wherein the acidic component comprises at least one of an acetate, glycine, malate, formate, or citrate buffer.
36. The kit of embodiment 32, further comprising a chaotropic salt.
37. The kit of embodiment 36, wherein the acidic component comprises a chaotropic salt.
38. The kit of embodiment 36, wherein the chaotropic salt comprises at least one of GuHCl and GITC.
39. The kit of embodiment 32, wherein the silica support comprises at least one of a particle, a bead, and a fiber.
40. The kit of embodiment 32, wherein the silica support is magnetic.
41. The kit of embodiment 32, wherein the pH of the acidic component is less than 5.
42. The kit of embodiment 41, wherein the pH of the acidic component is between 2.0 and 4.
43. A method comprising combining sulfonated DNA and a silica support in an acidic binding solution, wherein the acidic binding solution has a pH less than or equal to a isoelectric point (pH(I)) of the sulfonated DNA, and wherein sulfonated DNA is bound to the silica support, wherein the silica support preferably comprises at least one of a particle, a bead, and a fiber, wherein the silica support is preferably magnetic.

44. The method of embodiment 43, wherein the pH of the acidic binding solution is less than 5, preferably less than 4, preferably between about 2.0 and 4.

45. The method of embodiment 43 or embodiment 44, wherein the acidic binding solution comprises a chaotropic salt, wherein the chaotropic salt preferably comprises at least one of guanidine hydrochloride (GuHCl) and guanidine isothiocyanate (GITC).

46. The method of any one of embodiments 43-45, the method further comprises incubating single-stranded non-sulfonated DNA or partially-sulfonated DNA with a sulfonation reagent to produce the sulfonated DNA.

47. The method of embodiment 46, wherein the sulfonation reagent comprises at least one of ammonium bisulfite and sodium bisulfite.

48. The method of any one of embodiments 43-47, further comprising at least one of:
   i) washing a silica support bound to sulfonated DNA;
   ii) desulfonating the sulfonated DNA to form desulfonated DNA; and
   iii) eluting the desulfonated DNA from the silica support.

49. The method of embodiment 48, wherein incubating non-sulfonated DNA with a sulfonation reagent is in a sulfonation reaction solution having a pH at or above the pH(I) of the sulfonated DNA.

50. The method of embodiment 49, wherein at least a portion of the sulfonation reaction solution is removed from the sulfonated DNA prior to combining the sulfonated DNA and the silica support in the acidic binding solution.

51. The method of embodiment 50, wherein essentially all of the sulfonation reaction solution is removed from the sulfonated DNA prior to combining the sulfonated DNA and the silica support in the acidic binding solution.

52. The method of embodiment 50 or 51, wherein the at least a portion of the sulfonation reaction solution is removed from the sulfonated DNA by size exclusion filtration.

53. The method of any one of embodiments 49-52, wherein the acidic binding solution is formed by adding an acidic component to the sulfonated DNA in the sulfonation reaction solution.

54. The method of embodiment 53, wherein the acidic component is an acidic solution.

55. The method of embodiment 53 or 54, wherein the acidic component comprises at least one of an acidic acetate, glycine, malate, formate, or citrate solution.

56. The method of any one of embodiments 53-55, wherein the acidic component comprises a chaotropic salt, wherein the chaotropic salt preferably comprises at least one of GuHCl GITC.

57. A method of preparing desulfonated DNA, comprising:
   i) incubating single-stranded non-sulfonated DNA or partially-sulfonated DNA with a sulfonation reagent to produce sulfonated DNA in a sulfonation reaction mixture;
   ii) combining the sulfonation reaction mixture with:
      a) an acidic component;
      b) chaotropic salt; and
      c) a silica support
   to form an acidic binding solution, wherein the acidic binding solution has a pH less than or equal to an isoelectric point (pH(I)) of the sulfonated DNA, and wherein sulfonated DNA is bound to the silica support;
   iii) separating sulfonated DNA bound to the silica support from the acidic binding solution;
   iv) treating separated sulfonated DNA under conditions wherein the sulfonated DNA is desulfonated,
   preferably wherein the non-sulfonated DNA comprises one or more unmethylated cytosine nucleotides, and wherein the desulfonated DNA comprises one or more deoxyuracil nucleotides.

58. The method of embodiment 57, wherein treating separated sulfonated DNA under conditions wherein the sulfonated DNA is desulfonated comprises combining sulfonated DNA with a desulfonation solution.

59. The method of embodiment 58, wherein the desulfonation solution is combined with sulfonated DNA that is bound to the silica support.

60. A composition comprising sulfonated DNA and a silica support in an acidic binding solution comprising a chaotropic salt, wherein the acidic binding solution has a pH less than or equal to the pH(I) of the sulfonated DNA, and wherein the sulfonated DNA is bound to the silica support,
wherein the chaotropic salt preferably comprises at least one of GuHCl and GITC;
and wherein the acidic binding solution preferably comprises at least one of a acetate, glycine, malate, formate, or citrate buffer, preferably a citrate buffer.

61. The composition of embodiment 60, wherein the acidic binding solution comprises a bisulfite salt, preferably ammonium bisulfite.

62. The composition of embodiment 60 or embodiment 61, wherein the pH of the acidic binding solution is less than 5, preferably between 2.0 and 4.

63. A kit, comprising:
   i) a bisulfite reagent solution or components for preparing a bisulfite reagent solution, wherein the bisulfite reagent solution preferably has a pH that is greater than a pH(I) of sulfonated DNA;
   ii) a silica support; and
   iii) an acidic component, preferably an acidic solution, the acidic component having a pH less than or equal to the pH(I) of sulfonated DNA, wherein the acidic component preferably comprises at least one of an acetate, glycine, malate, formate, or citrate buffer, preferably citrate buffer.

64. The kit of embodiment 63, further comprising a chaotropic salt, wherein preferably the acidic component comprises a chaotropic salt, and wherein the chaotropic salt preferably comprises at least one of GuHCl and GITC.

65. The kit of embodiment 63 or 64, wherein the silica support comprises at least one of a particle, a bead, and a fiber.

66. The kit of any one of embodiments 63-65, wherein the silica support is magnetic.

67. The kit of any one of embodiments 63-66, wherein the pH of the acidic component is less than 5, preferably wherein the pH of the acidic component is between 2.0 and 4.

In certain preferred embodiments of any of the embodiments described herein, the single-stranded DNA is isolated from a sample, e.g., a biological sample. For example, in some preferred embodiments, the single-stranded DNA is isolated from a sample from a human subject, such as a subject having or suspected of having a cancer, e.g., from a plasma sample, a stool sample, or other sample from the subject. In other embodiments, the single-stranded DNA is synthetic. In preferred embodiments, single-stranded DNA is formed by exposing double-stranded DNA to denaturing conditions (e.g., alkaline conditions, high temperature, etc.) under which the base-paired DNA strands separate to form single strands. In some embodiments, the desulfonated DNA is measured, e.g., to measure one or more methylated DNA markers (MDMs) in the DNA. For example, any of the DNAs named in herein (e.g., in the Experimental section or in the Drawings, including MDMs disclosed in Tables 1-7, FIGS. 3, 7-13, 15A and 15B, 16, and 18) may be detected or measured, either singly or in combination, or in any sub-combination of 2, 3, 4, 5, 6, 7, 8, 9, 10, 11, 12, 13, 14, 15, 16, etc., from any type of sample (e.g., plasma, stool, tissue, etc.).

Other aspects and embodiments of the disclosure will be apparent in light of the following detailed description and accompanying figures.

BRIEF DESCRIPTION OF THE DRAWINGS

FIG. 8A provides a table showing strand recovery from different lots of ammonium bisulfite from binding reactions performed at low pH and at non-adjusted pH.

FIG. 8B provides a table showing strand recovery from different concentrations of ammonium bisulfite from binding reactions performed at low pH and at non-adjusted pH.

FIG. 9 provides a table showing the effects of a contaminant present in binding reactions performed at low pH and at non-adjusted pH.

FIG. 10 provides a table showing log of strands recovered using various silica beads using non-adjusted pH binding reactions.

FIG. 11 provides a table showing log of strands recovered using various silica beads using low pH binding reactions described in Example 1.

FIG. 12 provides a table showing strands recovered using binding reactions adjusted to acidic pHs ("BND pH") ranging from 4.85 down to 2.13.

FIG. 13 provides a table showing strands recovered for different sizes DNA molecules, and for different concentrations of DNA molecules, using non-adjusted or low pH binding reactions.

FIG. 14 shows a table comparing reaction conditions provided by Protocol 1, Protocol 2, and Protocol 3.

FIGS. 15A and 15B show tables comparing strand recoveries using Protocol 1, Protocol 2, and Protocol 3.

FIG. 16 shows a table with pairwise comparisons of strand recoveries shown in FIGS. 15A-15B for different methylation marker DNAs using Protocol 1, Protocol 2, and Protocol 3.

FIG. 18 shows a table comparing recoveries of different DNAs using unadjusted pH during the binding step, or using glycine, citrate, malate, or formate buffer to reduce the pH during binding the indicated sulfonated DNAs to silica beads.

DEFINITIONS

Figure 1A:
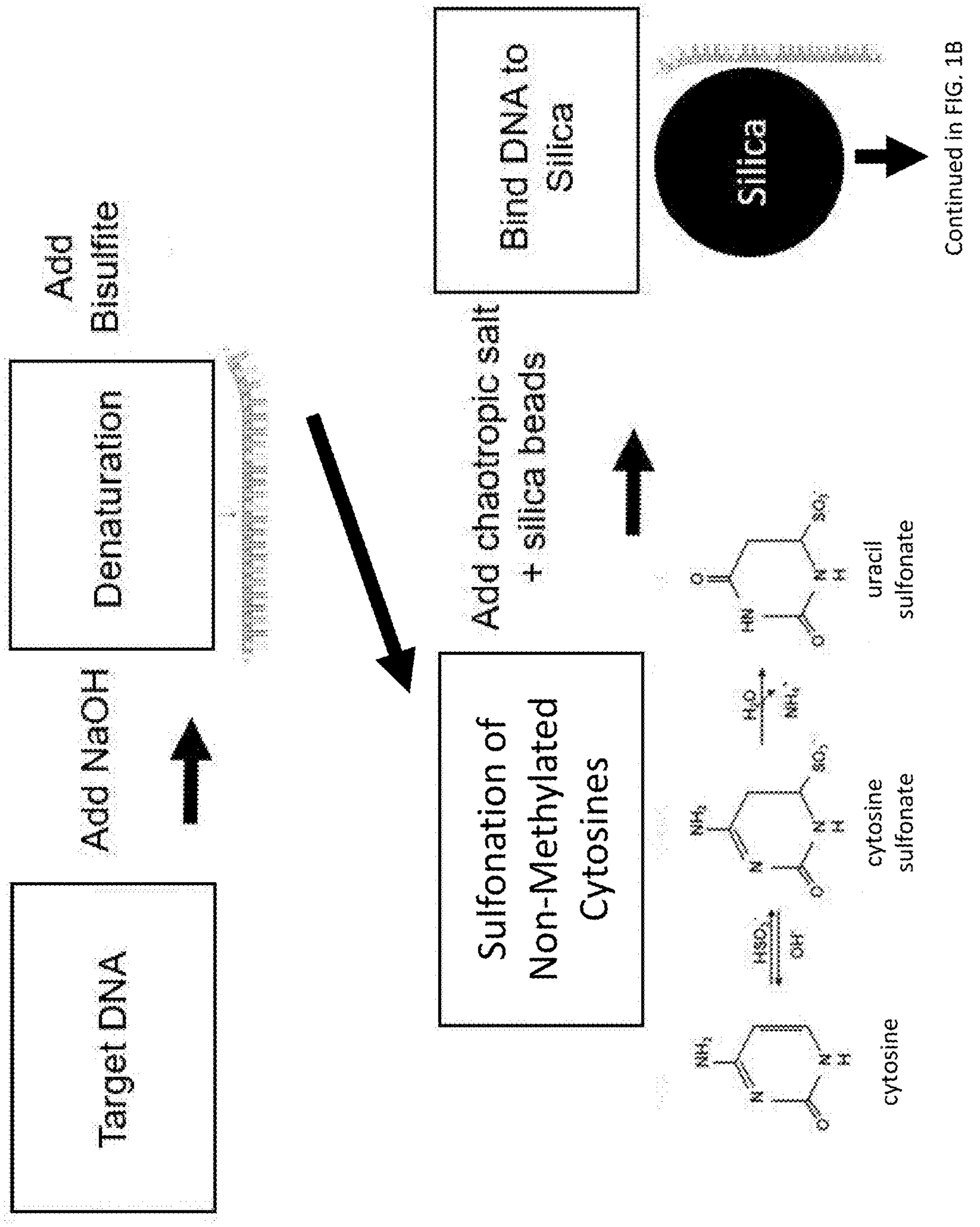
FIG. 1A and FIG. 1B provide an overview of one embodiment of a bisulfite treatment method comprising the methods disclosed herein.

Section headings as used in this section and the entire disclosure herein are merely for organizational purposes and are not intended to be limiting.

To facilitate an understanding of the present invention, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the technology may be readily combined, without departing from the scope or spirit of the technology.

The terms "comprise(s)," "include(s)," "having," "has," "can," "contain(s)," and variants thereof, as used herein, are intended to be open-ended transitional phrases, terms, or words that do not preclude the possibility of additional acts or structures. In addition, as used herein, the term "or" is an inclusive "or" operator and is equivalent to the term "and/or" unless the context clearly dictates otherwise. The term "based on" is not exclusive and allows for being based on additional factors not described unless the context clearly dictates otherwise.

The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

The transitional phrase "consisting essentially of" as used in claims in the present application limits the scope of a claim to the specified materials or steps "and those that do not materially affect the basic and novel characteristic(s)" of the claimed invention, as discussed in In re Herz, 537 F.2d 549, 551-52, 190 USPQ 461, 463 (CCPA 1976). For example, a composition "consisting essentially of" recited elements may contain an unrecited contaminant at a level such that, though present, the contaminant does not alter the function of the recited composition as compared to a pure composition, i.e., a composition "consisting of" the recited components.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

Unless otherwise defined herein, scientific and technical terms used in connection with the present disclosure shall have the meanings that are commonly understood by those of ordinary skill in the art. For example, any nomenclatures used in connection with, and techniques of, molecular biology and protein and nucleic acid chemistry and hybridization described herein are those that are well known and commonly used in the art. The meaning and scope of the terms should be clear; in the event, however of any latent ambiguity, definitions provided herein take precedent over any dictionary or extrinsic definition. Further, unless otherwise required by context, singular terms shall include pluralities and plural terms shall include the singular.

As used herein, a "DNA fragment" or "small DNA" or "short DNA" means a DNA that consists of no more than approximately 200 base pairs or nucleotides in length.

As used herein, "methylation" or "methylated," as used in reference to the methylation status of a cytosine, e.g., in a CpG locus, generally refers to the presence or absence of a methyl group at position 5 of the cytosine base (i.e., whether a particular cytosine is a 5-methyl cytosine). Methylation may be determined directly, e.g., as evidenced by routine methods for analysis of methylation status of cytosines, e.g., by determining the sensitivity (or lack thereof) of a particular C-residue to conversion to uracil by treatment with bisulfite. For example, a cytosine residue in a sample that is not converted to uracil when the sample is treated with bisulfite in a manner that would be expected to convert that residue if non-methylated (e.g., under conditions in which a majority or all of the non-methylated cytosines in the sample are converted to uracils) may generally be deemed "methylated".

As used herein, the terms "methyl cytosine," "methyl C," "methylated cytosine," "methylated C," and "meC" are used interchangeably and encompass both 5-methylcytosine (5 mC) and 5-hydroxymethyl cytosine (5 hmC).

The term "bisulfite reagent" refers to a reagent comprising bisulfite, disulfite, hydrogen sulfite, or combinations thereof, useful as disclosed herein to distinguish between methylated and unmethylated CpG dinucleotide sequences. Methods of said treatment are known in the art (e.g., PCT/EP2004/011715 and WO 2013/116375, each of which is incorporated by reference in its entirety). In some embodiments, bisulfite treatment is conducted in the presence of denaturing solvents such as but not limited to n-alkyleneglycol or diethylene glycol dimethyl ether (DME), or in the presence of dioxane or dioxane derivatives. In some embodiments the denaturing solvents are used in concentrations between 1% and 35% (v/v). In some embodiments, the bisulfite reaction is carried out in the presence of scavengers such as but not limited to chromane derivatives, e.g., 6-hydroxy-2,5,7,8,-tetramethylchromane 2-carboxylic acid or trihydroxybenzone acid and derivatives thereof, e.g., Gallic acid (see: PCT/EP2004/011715, which is incorporated by reference in its entirety). In certain preferred embodiments, the bisulfite reaction comprises treatment with ammonium hydrogen sulfite, also referred to as ammonium bisulfite, e.g., as described in WO 2013/116375.

As used herein, "sulfonated DNA" refers to a DNA comprising cytosines or uracils that have been sulfonated as a result of treatment with a sulfonation reagent, e.g. a bisulfite reagent. Sulfonated DNA may be partially sulfonated, such that the DNA comprises unmethylated cytosine(s) that have not been sulfonated to form uracil sulfonate, or the DNA may be completely sulfonated, such that every unmethylated (or otherwise unprotected) cytosine has been sulfonated to form uracil sulfonate. Sulfonated DNA may also be DNA synthesized, e.g., using standard nucleic acids synthesis chemistries, to mimic DNA that has been treated with a bisulfite reagent. For example, a strand of DNA may be synthesized from nucleotide monomers to form a strand that comprises one or more uracil sulfonate nucleotides.

As used herein, "unsulfonated DNA" refers to DNA that has not been treated with a sulfonation reagent, e.g., a bisulfite reagent, under conditions in which cytosines are converted to uracil sulfonate nucleotides. Unsulfonated DNA may comprise one or more unmethylated cytosine nucleotides. In preferred embodiments, unsulfonated DNA is free of uracil sulfonate nucleotides.

As used herein in reference to solutions or conditions for binding DNA to a solid support, the term "low pH" refers to a binding solution or condition that has a pH at or below the pH(I) of a solid support to which DNA, e.g., sulfonated DNA, is to be bound. In some embodiments, a low pH binding condition is provided by use of a binding solution comprising a binding agent, e.g., a chaotropic salt such as guanidine hydrochloride, in combination with an acidic component, e.g., a buffer having an acidic pH. In some embodiments, an acidic component is premixed with a binding agent before the binding mixture is combined with sulfonated DNA, while in some embodiments, an acidic component is combined with sulfonated DNA before or after the binding agent, is combined with the sulfonated DNA.

As used herein in reference to solutions or conditions for binding sulfonated DNA to a solid support, the terms "non-adjusted pH," "standard pH," and "high pH" are used interchangeably, and refer to binding reaction solutions or conditions that do not include an acidic component to reduce the pH of the binding solution or condition relative to the pH of binding solutions comprising only the sulfonated DNA and the binding agent, e.g., GuHCl. Generally, non-adjusted pH binding solutions have in a pH at or above the pH(I) of the solid support, especially a silica support. In some embodiments, a non-adjusted pH binding solution is a mixture comprising some or all of the sulfonation reagent used to sulfonate the sample of DNA, the sulfonated DNA, and the binding agent, e.g., GuHCl. In some embodiments, the pH of the non-adjusted binding solution is at or near the pH of the sulfonation reagent alone.

The term "sample" as used herein is used in its broadest sense. For example, a sample suspected of containing a human gene or chromosome or sequences associated with a human chromosome may comprise a cell, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support), cell-free DNA (e.g., circulating cell free DNA from plasma; fragmented DNA from a bodily fluid, such as plasma, urine, stool, etc.); DNA isolated from exosomes or other microvesicles, e.g., from a body fluid, and the like. In some embodiments, it is meant to include a specimen or culture (e.g., microbiological culture), whereas in other embodiments, it is meant to include both biological and environmental samples (e.g., suspected of comprising a target sequence, gene or template). In some embodiments, a sample may include a specimen of synthetic origin. Samples may be unpurified or may be partially or completely purified or otherwise processed. A sample "suspected of containing" a nucleic acid may contain or not contain the target nucleic acid molecule.

The present technology is not limited by the type of biological sample used or analyzed. The present technology is useful with a variety of biological samples including, but not limited to, tissue (e.g., organ (e.g., heart, liver, brain, lung, stomach, intestine, spleen, kidney, pancreas, and reproductive organs), glandular, skin, and muscle), cell (e.g., blood cell (e.g., lymphocyte or erythrocyte), muscle cell, tumor cell, and skin cell), gas, bodily fluid (e.g., blood or portion thereof, serum, plasma, urine, semen, saliva, etc.), or solid (e.g., stool) samples obtained from a human (e.g., adult, infant, or embryo) or animal (e.g., cattle, poultry, mouse, rat, dog, pig, cat, horse, and the like). In some embodiments, biological samples may be solid food and/or feed products and/or ingredients such as dairy items, vegetables, meat and meat by-products, and waste. Biological samples may be obtained from all of the various families of domestic animals, as well as feral or wild animals, including, but not limited to, such animals as ungulates, bear, fish, lagomorphs, rodents, pinnipeds, etc.

Biological samples also include biopsies and tissue sections (e.g., biopsy or section of tumor, growth, rash, infection, or paraffin-embedded sections), medical or hospital samples (e.g., including, but not limited to, blood samples, saliva, buccal swab, cerebrospinal fluid, pleural fluid, milk, colostrum, lymph, sputum, vomitus, bile, semen, oocytes, cervical cells, amniotic fluid, urine, stool, hair, and sweat), laboratory samples (e.g., subcellular fractions), and forensic samples (e.g., blood or tissue (e.g., spatter or residue), hair and skin cells containing nucleic acids), and archeological samples (e.g., fossilized organisms, tissue, or cells).

Environmental samples include, but are not limited to, environmental material such as surface matter, soil, water (e.g., freshwater or seawater), algae, lichens, geological samples, air containing materials containing nucleic acids, crystals, and industrial samples, as well as samples obtained from food and dairy processing instruments, apparatus, equipment, utensils, disposable and non-disposable items.

Samples may be prepared by any desired or suitable method. In some embodiments, nucleic acids are analyzed directly from bodily fluids, stool, or other samples using the methods and systems described in U.S. Pat. Nos. 9,000,146; and 10,047,390, each of which is herein incorporated by reference in its entirety for all purposes.

The above-described examples are not, however, to be construed as limiting the sample (e.g., suspected of comprising a target sequence, gene or template (e.g., the presence or absence of which can be determined using the compositions and methods of the present technology)) types applicable to the present technology.

The term "target," when used in reference to a nucleic acid detection or analysis method, refers to a nucleic acid having a particular sequence of nucleotides to be detected or analyzed, e.g., in a sample suspected of containing the target nucleic acid. In some embodiments, a target is a nucleic acid having a particular sequence for which it is desirable to determine a methylation status. When used in reference to the polymerase chain reaction, "target" generally refers to the region of nucleic acid bounded by the primers used for polymerase chain reaction. Thus, the "target" is sought to be sorted out from other nucleic acid sequences that may be present in a sample. A "segment" is defined as a region of nucleic acid within the target sequence. The term "sample template" refers to nucleic acid originating from a sample that is analyzed for the presence of a target.

The term "template" as used in reference to a nucleic acid strand of a flap structure, e.g., an invasive cleavage structure, refers to the strand to which upstream and downstream nucleic acids or nucleic acid regions hybridize to form an invasive cleavage structure. While a template strand may serve as template for extension of a primer by a polymerase, e.g., in a PCR flap endonuclease assay, use of the term is not limited to polymerizing assays or reactions.

As used herein, the term "nucleic acid molecule" refers to any nucleic acid containing molecule, including but not limited to, DNA or RNA. The term encompasses sequences that include any of the known base analogs of DNA and RNA including, but not limited to, 4 acetylcytosine, 8-hydroxy-N6-methyladenosine, aziridinylcytosine, pseudoisocytosine, 5-(carboxyhydroxyl-methyl) uracil, 5-fluorouracil, 5-bromouracil, 5-carboxymethylaminomethyl-2-thiouracil, 5-carboxymethyl-aminomethyluracil, dihydrouracil, inosine, N6-isopentenyladenine, 1-methyladenine, 1-methylpseudo-uracil, 1-methylguanine, 1-methylinosine, 2,2-dimethyl-guanine, 2-methyladenine, 2-methylguanine, 3-methyl-cytosine, 5-methylcytosine, 5-hydroxymethylcytosine, 5-carboxylcytosine, 5-formylcytosine, N6-methyladenine, 7-methylguanine, 5-methylaminomethyluracil, 5-methoxy-amino-methyl-2-thiouracil, beta-D-mannosylqueosine, 5'-methoxycarbonylmethyluracil, 5-methoxyuracil, 2-methylthio-N-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

A nucleic acid sequence or molecule may be DNA or RNA, of either genomic or synthetic origin, that may be single or double stranded, and represent the sense or antisense strand. Thus, nucleic acid sequence may be dsDNA, ssDNA, mixed ssDNA, mixed dsDNA, dsDNA made into ssDNA (e.g., through melting, denaturing, helicases, etc.), A-, B-, or Z-DNA, triple-stranded DNA, RNA, ssRNA, dsRNA, mixed ss and dsRNA, dsRNA made into ssRNA (e.g., via melting, denaturing, helicases, etc.), messenger RNA (mRNA), ribosomal RNA (rRNA), transfer RNA (tRNA), catalytic RNA, snRNA, microRNA, or protein nucleic acid (PNA).

The present technology is not limited by the type or source of nucleic acid (e.g., sequence or molecule (e.g., target sequence and/or oligonucleotide)) utilized. For example, the nucleic acid sequence may be amplified or created sequence (e.g., amplification or creation of nucleic acid sequence via synthesis (e.g., polymerization (e.g., primer extension (e.g., RNA-DNA hybrid primer technology)) and reverse transcription (e.g., of RNA into DNA)) and/or amplification (e.g., polymerase chain reaction (PCR), rolling circle amplification (RCA), nucleic acid sequence based amplification (NASBA), transcription mediated amplification (TMA), ligase chain reaction (LCR), cycling probe technology, Q-beta replicase, strand displacement amplification (SDA), branched-DNA signal amplification (bDNA), hybrid capture, and helicase dependent amplification).

As used herein, the term "process control" refers to an exogenous molecule, e.g., an exogenous nucleic acid added to a sample prior to extraction of target DNA that can be measured post-extraction to assess the efficiency of the process and be able to determine success or failure modes. The nature of the process control nucleic acid used is usually dependent on the assay type and the material that is being measured. For example, if the assay being used is for detection and/or quantification of double stranded DNA or mutations in it, then double stranded DNA process controls are typically spiked into the samples before extraction. Similarly, for assays that monitor mRNA or microRNAs, the process controls used are typically either RNA transcripts or synthetic RNA. Process controls typically aid in assessment of the efficiency of a process and in determination of success or failure of processes and process steps.

As used herein in reference to non-target DNA, the term "exogenous" refers to non-target DNA that is isolated and purified from a source other than the source or sample containing the target DNA. For example, purified fish DNA is exogenous DNA with respect to a sample comprising human target DNA, e.g., as described in U.S. Pat. No. 9,212,392, which is incorporated herein by reference. Exogenous DNA need not be from a different organism than the target DNA. For example, purified fish DNA obtained commercially would be exogenous if added to a reaction configured to detect a target nucleic acid in a sample from a particular fish. In preferred embodiments, exogenous DNA is selected to be undetected by an assay configured to detect and/or quantify the target nucleic acid in the reaction into which the exogenous DNA is added.

As used herein the term "fish DNA" refers to bulk (e.g., genomic) DNA isolated from fish, e.g., as described in U.S. Pat. No. 9,212,392. Bulk purified fish DNA is commercially available, e.g., provided in the form of cod and/or herring sperm DNA (Roche Applied Science, Mannheim, Germany) or salmon DNA (USB/Affymetrix). "Fish DNA" is distinct from any particular gene from a fish that is in isolated form, e.g., that has been separately synthesized or that has been separated from the other DNA of the fish genome.

As used herein, the term "zebrafish DNA" refers to DNA isolated from Danio rerio, or created in vitro (e.g., enzymatically, synthetically) to have a sequence of nucleotides found in DNA from Danio rerio. In preferred embodiments, the zebrafish DNA is a methylated DNA added as a detectable control DNA, e.g., a process control for verifying DNA recovery through sample processing steps. In particular, zebrafish DNA comprising at least a portion of the RASSF1 gene finds use as a process control, e.g., for human samples, as described in WO 2018/017710A1, which is incorporated herein by reference, and which describes use of zebrafish DNA as a process control for human samples. As used herein, "ZFRASSF1" refers to a process control comprising at least a portion of the zebrafish RASSF1 gene.

As used herein, the terms "recovery" and "recovered" as used in reference to strands of nucleic acid refers to the amount or number of strands of DNA measured in sample after a process (e.g., a complete bisulfite conversion process) or after one or more process steps (e.g., matrix binding of nucleic acids, followed by elution of the bound strands). In some embodiments, the strands recovered are compared to a reference value, e.g., an amount or number of strands added or expected to be present in a sample prior to processing, or an amount measured in or expected to be present in a reference sample.

As used herein, the term "kit" refers to any delivery system for delivering materials. In the context of nucleic acid purification systems and reaction assays, such delivery systems include systems that allow for the storage, transport, or delivery of reagents and devices (e.g., chaotropic salts, particles, buffers, denaturants, oligonucleotides, filters etc. in the appropriate containers) and/or supporting materials (e.g., sample processing or sample storage vessels, written instructions for performing a procedure, etc.) from one location to another. For example, kits include one or more enclosures (e.g., boxes) containing the relevant reaction reagents and/or supporting materials. As used herein, the term "fragmented kit" refers to a delivery system comprising two or more separate containers that each contains a subportion of the total kit components. The containers may be delivered to the intended recipient together or separately. For example, a first container may contain materials for sample collection and a buffer, while a second container contains capture oligonucleotides and denaturant. The term "fragmented kit" is intended to encompass kits containing Analyte specific reagents (ASR's) regulated under section 520 (e) of the Federal Food, Drug, and Cosmetic Act, but are not limited thereto. Indeed, any delivery system comprising two or more separate containers that each contains a subportion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

The term "system" as used herein refers to a collection of articles for use for a particular purpose. In some embodiments, the articles comprise instructions for use, as information supplied on e.g., an article, on paper, online (e.g., at a website or web address) on recordable media (e.g., diskette, CD, DVD, flash drive, etc.). In some embodiments, instructions direct a user to an online location, e.g., a website for viewing, hearing, and/or downloading instructions. In some embodiments, instructions or other information are provided as an application ("app"), e.g., for a computer or for a mobile device, such as a smart phone.

As used herein, the term "information" refers to any collection of facts or data. In reference to information stored or processed using a computer system(s), including but not limited to internets, the term refers to any data stored in any format (e.g., analog, digital, optical, etc.). As used herein, the term "information related to a subject" refers to facts or data pertaining to a subject (e.g., a human, plant, or animal). The term "genomic information" refers to information pertaining to a genome including, but not limited to, nucleic acid sequences, genes, allele frequencies, RNA expression levels, protein expression, phenotypes correlating to genotypes, etc. "Allele frequency information" refers to facts or data pertaining to allele frequencies, including, but not limited to, allele identities, statistical correlations between the presence of an allele and a characteristic of a subject (e.g., a human subject), the presence or absence of an allele in an individual or population, the percentage likelihood of an allele being present in an individual having one or more particular characteristics, etc.

DETAILED DESCRIPTION OF THE INVENTION

Preferred methods and materials are described below, although methods and materials similar or equivalent to those described herein can be used in practice or testing of the present disclosure. All publications, patent applications, patents and other references mentioned herein are incorporated by reference in their entirety. The materials, methods, and examples disclosed herein are illustrative only and not intended to be limiting.

The technologies provided herein relate to methods for improving post-modification recovery of DNA that has been treated with a sulfonation reagent. In particular, the technology provides methods of binding sulfonated DNA to charged surfaces, e.g., to silica surfaces or supports, e.g., a surface of an assay well or slide, fibers, particles, beads, and the like. While the technology is discussed in reference to certain materials and forms of supports, e.g., silica in the form of a bead, it will be understood that the technology is applicable to other support materials, and to supports of any form or configuration, including fibers, particles, tubes, etc.

The methods provide conditions that promote a highly stable binding of the sulfonated DNA to the beads. This facilitates the efficient recovery of bisulfite-treated DNA despite the highly basic reaction conditions of desulfonation that one of skill in the art would expect to disrupt the interaction of the DNA with the beads. By combination of the innovative steps provided herein, the technology provides methods for preparing bisulfite-converted DNA with improved recovery of the input DNA.

The technology is related to the experimental findings described below and developed in the experimental examples. These examples describe the development and testing of reagents used for the analysis of the methylation state of a nucleic acid. In particular, the technology is related to binding solutions that have an acidic pH, such that the pH of the binding buffer is below the isoelectric point pH(I) of both silica and uracil sulfonate-rich DNA, thereby promoting binding of the sulfonated DNA to silica.

Common sulfonation reagents include sodium bisulfite and ammonium bisulfite. In the examples below, ammonium bisulfite is used but the principles of the technology are readily applicable to any DNA treated in a manner that creates a charge, e.g., a highly negative charge, across the molecule. For example, DNA treated with other sulfonation reagents, e.g., sodium bisulfite, find use with the present technology.

Figure 2:
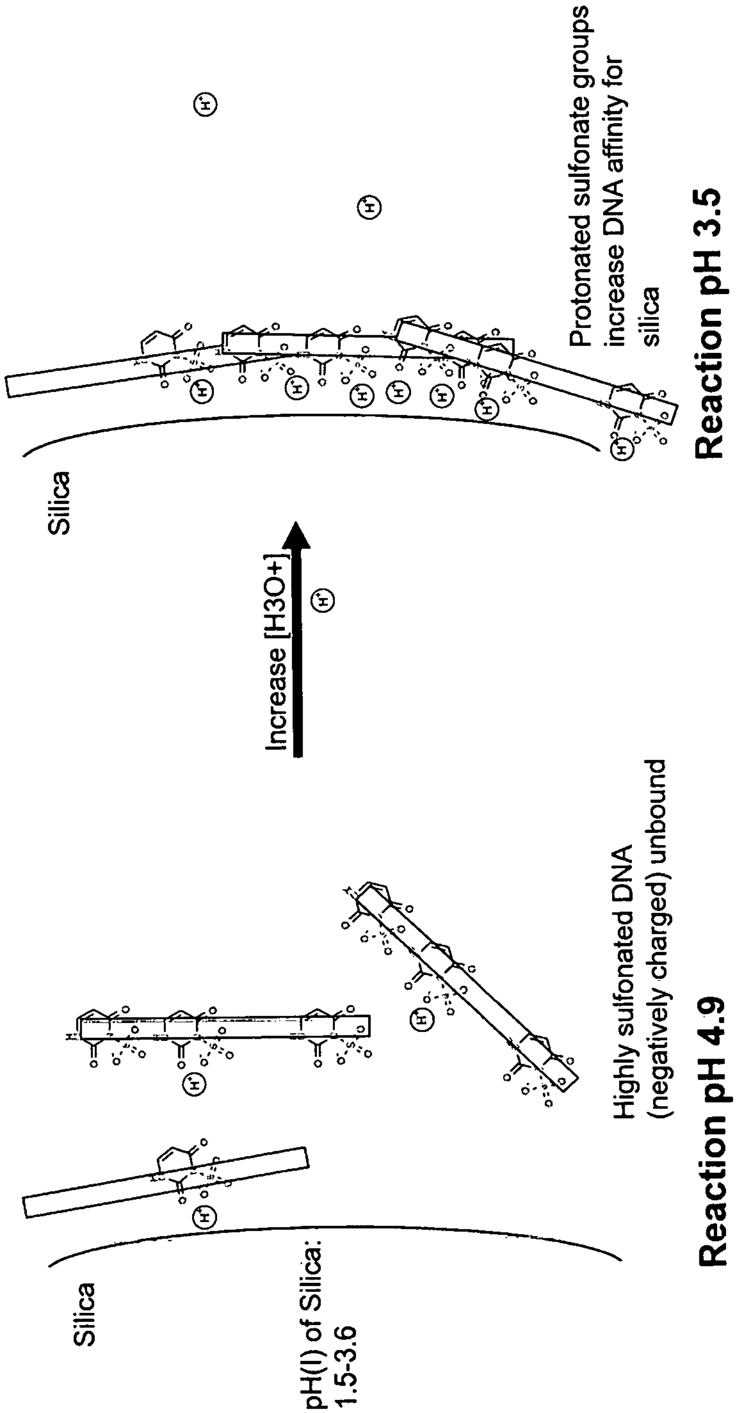
FIG. 2 is a schematic of the proposed binding mechanism.

Without addition of an acid, the pH of a sulfonation reaction is largely determined by the ammonium bisulfite, which typically has a pH that is above the pH(I) of silica (as shown schematically in FIG. 2), and at or above the pH(I) of sulfonated DNA. However, when the pH of a binding reaction is above the pH(I) of the silica (or other support material) and/or the DNA, electrostatic repulsion may prevent complete binding of the DNA to the silica. While not limiting the technology to any particular mechanism of action, it is observed that conducting the binding reaction at an acidic pH, e.g., by addition of acid to the sulfonated DNA-silica bead mixture, may neutralize the silica and protonate the uracil sulfonate groups of the DNA, thereby reducing electrostatic repulsion and promoting silica-sulfonated DNA interaction.

DNA suitable for use with the technology is not limited to DNA isolated by any particular method, and suitable DNA may be prepared in a number of ways, including by the use of commercial kits, columns, and the like. Exemplary methods of isolating DNA from samples, e.g., from a subject, are described below.

Stool DNA Isolation

In some embodiments, DNA may be isolated from a stool sample. An exemplary embodiment of isolating DNA from stool that is suitable for use with the present technology is found in U.S. Pat. No. 9,000,146, which is incorporated herein by reference. Briefly, the stool sample is homogenized with a buffer, the solids are removed, e.g., by centrifugation, and specific target DNAs are captured from the resulting clarified supernatant using particles or beads comprising oligonucleotides complementary to the target DNA(s). Target DNAs bound to the capture oligonucleotides are separated from the solution, e.g., by use of magnetic field to collect magnetic beads, and the captured DNAs are optionally washed with buffer prior to elution from the capture oligonucleotides, e.g., using denaturing conditions.

Cell Line and Cell Media DNA

For cell lines, cell-free genomic DNA may be isolated from cell-conditioned media using, for example, the "Maxwell® RSC ccfDNA Plasma Kit (Promega Corp., Madison, WI). Following the kit protocol, 1 mL of cell conditioned media (CCM) is used in place of plasma, and processed according to the kit procedure. The elution volume is 100 μL, of which 70 μL are generally used for bisulfite conversion.

Blood or Plasma DNA

An exemplary procedure for isolating DNA from a 4 mL sample of plasma, e.g., from a human blood sample, is as follows:

- To a 4 mL sample of plasma, 300 μL of Proteinase K (20 mg/mL) is added and mixed.
- Add 3 μL of 1 μg/μL of Fish DNA to the plasma-proteinase K mixture.
- Add 2 mL of plasma lysis buffer to plasma.
  - Plasma lysis buffer is:
    - 4.3 M guanidine thiocyanate
    - 10% IGEPAL CA-630 (Octylphenoxy poly(ethyleneoxy)ethanol, branched)
      - (5.3 g of IGEPAL CA-630 combined with 45 mL of 4.8 M guanidine thiocyanate)
- Incubate mixtures at 55 °C for 1 hour with shaking at 500 rpm.
- Add and mix:
  - 3 mL of plasma lysis buffer
  - 200 μL magnetic silica binding beads (16 μg of beads/μL)
  - Add 2 mL of 100% isopropanol
    - (optionally mix after each addition and/or optionally pre-mix the lysis buffer and isopropanol before adding to the mixture)
- Incubate at 30 °C for 30 minutes with shaking at 500 rpm.
- Place tube(s) on magnet and let the beads collect. Aspirate and discard the supernatant.
- Add 7504 GuHCl-EtOH to vessel containing the binding beads and mix.
  - GuHCl-EtOH wash buffer is:
    - 3 M GuHCl (guanidine hydrochloride)
    - 57% EtOH (ethyl alcohol)
- Shake at 400 rpm for 1 minute.
- Transfer samples to a deep well plate or 2 mL microcentrifuge tubes.
- Place tubes on magnet and let the beads collect for 10 minutes. Aspirate and discard the supernatant.
- Add 1000 μL wash buffer (10 mM Tris HCl, 80% EtOH) to the beads, and incubate at 30 °C for 3 minutes with shaking.
- Place tubes on magnet and let the beads collect. Aspirate and discard the supernatant.
- Add 500 μL wash buffer to the beads and incubate at 30 °C for 3 minutes with shaking.

Place tubes on magnet and let the beads collect. Aspirate and discard the supernatant.

Add 250 μL wash buffer and incubate at 30 °C for 3 minutes with shaking.

Place tubes on magnet and let the beads collect. Aspirate and discard the remaining buffer.

dd 250 μL wash buffer and incubate at 30 °C for 3 minutes with shaking.

Place tubes on magnet and let the beads collect. Aspirate and discard the remaining buffer.

Dry the beads at 70 °C for 15 minutes, with shaking.

Add 125 μelution buffer (10 mM Tris HCl, pH 8.0, 0.1 mM EDTA) to the beads and incubate at 65 °C for 25 minutes with shaking.

Place tubes on magnet and let the beads collect for 10 minutes.

Aspirate and transfer the supernatant containing the DNA to a new vessel or tube.

DNA Sulfonation and Purification

Figure 1B:
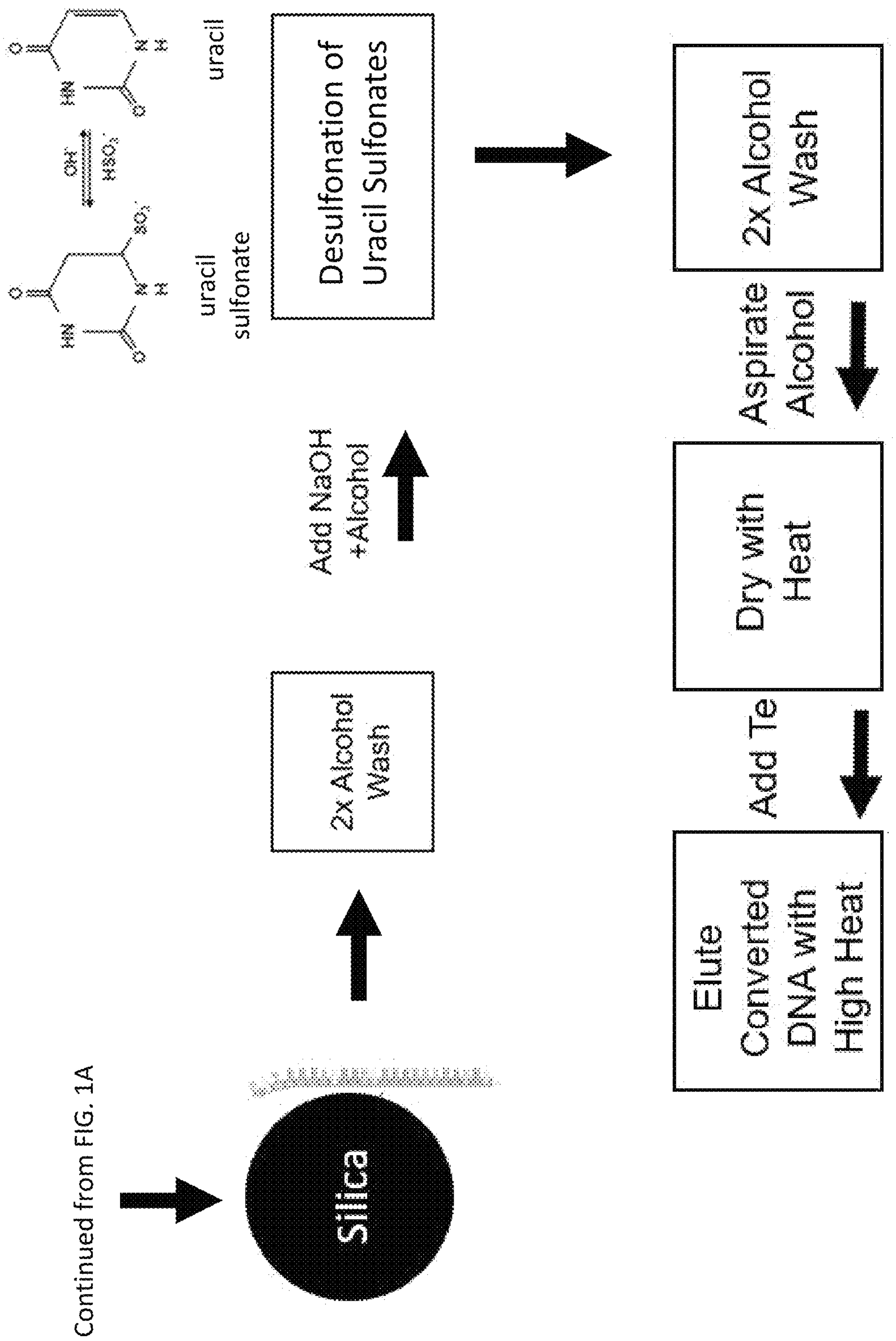

In a typical bisulfite treatment method, in the bisulfite treatment step un-methylated cytosine bases undergo deamination and sulfonation, becoming negatively-charged uracil sulfonates (FIGS. 1A-1B). To remove conversion reagents, sulfonated DNA samples may be alcohol precipitated or isolated, e.g., by gel filtration. Sulfonated DNA may also be bound to a support such as silica, e.g., silica-coated surfaces of reaction vessels, silica particles or fibers, paramagnetic silica beads, etc., by addition of chaotropic salt, e.g., a guanidine salt such as guanidine hydrochloride (GuHCl) or guanidine isothiocyanate (GITC), at about, e.g., 6 to 7 M concentration. Other chaotropic binding agents for promoting the binding of denatured DNA to a solid matrix include iodide, perchlorate, and trichloroacetate.

A typical method of bisulfite treatment of DNA (without a low pH binding step of the present technology) is as follows:

I. Sulfonation of DNA using ammonium hydrogen sulfite

1. In each tube, combine 64 μL DNA, 7 μL 1 N NaOH, and 9 μL of carrier solution containing 0.2 mg/mL BSA and 0.25 mg/mL of fish DNA.
2. Incubate at 42 °C for 20 minutes.
3. Add 120 μL of 45% ammonium hydrogen sulfite and incubate at 66° for 75 minutes.
4. Incubate at 4 °C for 10 minutes.

II. Desulfonation using magnetic beads

Materials

Magnetic beads (Promega MagneSil Paramagnetic Particles, Promega catalogue number AS1050, 16 μg/μL).

Binding buffer: 6.5-7 M guanidine hydrochoride.

Post-conversion Wash buffer: 80% ethanol with 10 mM Tris HCl (pH 8.0).

Desulfonation buffer: 70% isopropyl alcohol, 0.1 N NaOH was selected for the desulfonation buffer.

Samples are mixed using any appropriate device or technology to mix or incubate samples at the temperatures and mixing speeds essentially as described below. For example, a Thermomixer (Eppendorf) can be used for the mixing or incubation of samples. An exemplary desulfonation is as follows:

1. Mix bead stock thoroughly by vortexing bottle for 1 minute.
2. Aliquot 50 μL of beads into a 2.0 mL tube (e.g., from USA Scientific).
3. Add 750 μL of binding buffer to the beads.
4. Add 150 μL of sulfonated DNA from step I.
5. Mix (e.g., 1000 RPM at 30 °C for 30 minutes).
6. Place tube on the magnet stand and leave in place for 5 minutes. With the tubes on the stand, remove and discard the supernatant.
7. Add 1,000 μL of wash buffer. Mix (e.g., 1000 RPM at 30 °C for 3 minutes).
8. Place tube on the magnet stand and leave in place for 5 minutes. With the tubes on the stand, remove and discard the supernatant.
9. Add 250 μL of wash buffer. Mix (e.g., 1000 RPM at 30 °C for 3 minutes).
10. Place tube on magnetic rack; remove and discard supernatant after 1 minute.
11. Add 200 μL of desulfonation buffer. Mix (e.g., 1000 RPM at 30 °C for 5 minutes).
12. Place tube on magnetic rack; remove and discard supernatant after 1 minute.
13. Add 250 μL of wash buffer. Mix (e.g., 1000 RPM at 30 °C for 3 minutes).
14. Place tube on magnetic rack; remove and discard supernatant after 1 minute.
15. Add 250 μL of wash buffer to the tube. Mix (e.g., 1000 RPM at 30 °C for 3 minutes).
16. Place tube on magnetic rack; remove and discard supernatant after 1 minute.
17. Incubate all tubes at 30 °C with the lid open for 15 minutes.
18. Remove tube from magnetic rack and add 70 μL of elution buffer directly to the beads.
19. Incubate the beads with elution-buffer (e.g., 1000 RPM at 40 °C for 45 minutes).
20. Place tubes on magnetic rack for about one minute; remove and save the supernatant.

The converted DNA is then used in a detection assay, e.g., a pre-amplification and/or flap endonuclease assays, as described below.

Magnetic Silica Beads

The technology provided herein relates to the bisulfite treatment and isolation of DNA for a quantitative measure of DNA methylation. In some embodiments, magnetic beads are used for the treatment and isolation of DNA, e.g., beads comprising a magnetic core and a silica coating. The silica coating binds DNA and the magnetic core provides an efficient way to concentrate and isolate the beads (and bound DNA) using a magnet. In some embodiments, the silica-coated magnetic beads are MagneSil Paramagnetic Particles (Promega, Madison, WI; catalogue number AS1220 or AS640A, promega.com).

The technology is not limited to any particular type of magnetic bead. Embodiments of the technology described herein make use of any magnetic beads (e.g., paramagnetic beads) that have an affinity for nucleic acids. In some embodiments, the magnetic beads have a magnetite (e.g., $Fe_3O_4$) core and a coating comprising silicon dioxide ($SiO_2$). The bead structure (e.g., size, porosity, shape) and composition of the solution in which a nucleic acid is bound to the bead can be altered to bind different types (e.g., DNA or RNA in single stranded, double stranded, or other forms or conformations; nucleic acids derived from a natural source, synthesized chemically, synthesized enzymatically (e.g., by PCR)) and sizes of nucleic acids (e.g., small oligomers, primers, genomic, plasmids, fragments, e.g., consisting of 200 or fewer bases) selectively. These characteristics of the beads affect the binding and elution of the nucleic acids to the beads. Related technologies are described, e.g., in U.S. Pat. Nos. 6,194,562; 6,270,970; 6,284,470; 6,368,800; 6,376,194, each incorporated herein by reference. Also contemplated are magnetic beads coated with, e.g., organosilane (as described in U.S. Pat. No. 4,554,088); carboxylated polyacrylate (as described in U.S. Pat. No. 5,648,124); cellulose (as described in U.S. patent application Ser. No. 10/955,974); hydroxysilane (as described in U.S. patent application Ser. No. 11/459,541); and hydrophobic aliphatic ligands (as described in U.S. patent application Ser. No. 12/221,750), each incorporated herein by reference for all purposes.

The technology is not limited to a particular size of magnetic bead. Accordingly, embodiments of the technology use magnetic beads of a number of different sizes. Smaller beads provide more surface area (per weight unit basis) for adsorption, but smaller beads are limited in the amount of magnetic material that can be incorporated in the bead core relative to a larger bead. In some embodiments, the particles are distributed over a range of sizes with a defined average or median size appropriate for the technology for which the beads are used. In some embodiments, the particles are of a relatively narrow monomodal particle size distribution.

In some embodiments, the beads that find use in the present technology have pores that are accessible from the exterior of the particle. Such pores have a controlled size range that is sufficiently large to admit a nucleic acid, e.g., a DNA fragment, into the interior of the particle and to bind to the interior surface of the pores. The pores are designed to provide a large surface area that is capable of binding a nucleic acid. Moreover, in one aspect the technology is not limited to any particular method of nucleic acid (e.g., DNA) binding and/or isolation. Thus, in some embodiments, aspects of the technology relating to the bisulfite reaction are combined with other suitable methods of DNA isolation (e.g., precipitation, column chromatography (e.g., a spin column), etc.

The beads (and bound material) are removed from a mixture using a magnetic field. In some embodiments, other forms of external force in addition to a magnetic field are used to isolate the biological target substance according to the present technology. For example, suitable additional forms of external force include, but are not limited to, gravity filtration, vacuum filtration, and centrifugation.

Embodiments of the technology apply an external magnetic field to remove the complex from the medium. Such a magnetic field can be suitably generated in the medium using any one of a number of different known means. For example, one can position a magnet on the outer surface of a container of a solution containing the beads, causing the particles to migrate through the solution and collect on the inner surface of the container adjacent to the magnet. The magnet can then be held in position on the outer surface of the container such that the particles are held in the container by the magnetic field generated by the magnet, while the solution is decanted out of the container and discarded. A second solution can then be added to the container, and the magnet removed so that the particles migrate into the second solution. Alternatively, a magnetizable probe could be inserted into the solution and the probe magnetized, such that the particles deposit on the end of the probe immersed in the solution. The probe could then be removed from the solution, while remaining magnetized, immersed into a second solution, and the magnetic field discontinued permitting the particles go into the second solution. Commercial sources exist for magnets designed to be used in both types of magnetic removal and transfer techniques described in general terms above. See, e.g., MagneSphere Technology Magnetic Separation Stand or the PolyATract Series 9600™ Multi-Magnet, both available from Promega Corporation; Magnetight Separation Stand (Novagen, Madison, Wis.); or Dynal Magnetic Particle Concentrator (Dynal, Oslo, Norway). Some embodiments comprise use of a magnetic device according to U.S. patent application Ser. No. 13/089,116, which is incorporated herein by reference in its entirety for all purposes. Furthermore, some embodiments contemplate the use of a "jet channel" or pipet tip magnet separation (e.g., as described in U.S. Pat. Nos. 5,647,994 and 5,702,950). Some embodiments contemplate the use of an immersed probe approach (e.g, as described in U.S. Pat. Nos. 6,447,729 and 6,448,092), e.g., as exemplified by the KingFisher systems commercially available from Thermo Scientific.

Quantitation of DNA Strands

In the examples described herein, strand recovery was measured using flap endonuclease assays. Exemplary methods for extracting sample nucleic acids, e.g., from blood, and for quantitating strands of bisulfite-converted DNA and unconverted DNA are described, for example, in U.S. Pat. No. 10,648,025, which is incorporated herein by reference for all purposes.

QuARTS Assay

An exemplary method of quantifying DNA strands produced according to the technology is the QuARTS flap assay technology. The QuARTS technology combines a polymerase-based target DNA amplification process with an invasive cleavage-based signal amplification process. The technology is described, e.g., in U.S. Pat. Nos. 8,361,720; 8,715,937; 8,916,344; and 9,212,392, and U.S. patent application Ser. No. 15/841,006, each of which is incorporated herein by reference. Fluorescence signal generated by the QuARTS reaction is monitored in a fashion similar to real-time PCR and permits quantitation of the amount of a target nucleic acid in a sample.

An exemplary QuARTS reaction typically comprises approximately 400-600 nmol/L (e.g., 500 nmol/L) of each primer and detection probe, approximately 100 nmol/L of the invasive oligonucleotide, approximately 600-700 nmol/L of each FRET cassette (FAM, e.g., as supplied commercially by Hologic, Inc.; HEX, e.g., as supplied commercially by BioSearch Technologies; and Quasar 670, e.g., as supplied commercially by BioSearch Technologies), 6.675 ng/μL FEN-1 endonuclease (e.g., Cleavase® 2.0, Hologic, Inc.), 1 unit Taq DNA polymerase in a 30 μL reaction volume (e.g., GoTaq® DNA polymerase, Promega Corp., Madison, WI), 10 mmol/L 3-(n-morpholino) propanesulfonic acid (MOPS), 7.5 mmol/L $MgCl_2$, and 250 μmol/L of each dNTP. Exemplary QuARTS cycling conditions are as shown in the table below. In some applications, analysis of the quantification cycle ($C_q$) provides a measure of the initial number of target DNA strands (e.g., copy number) in the sample.

| Stage | Temp/Time | # of Cycles |
|---|---|---|
| Denaturation | 95° C./3' | 1 |
| Amplification 1 | 95° C./20"<br>67° C./30"<br>70° C./30" | 10 |
| Amplification 2 | 95° C./20"<br>53° C./1'<br>70° C./30" | 37 |
| Cooling | 40° C./30" | 1 |

Multiplex Targeted Pre-amplification of Large-Volume Bisulfite-Converted DNA

To pre-amplify most or all of the bisulfite-treated DNA from an input sample, a large volume of the treated DNA may be used in a single, large-volume multiplex amplification reaction. For example, DNA is extracted from a cell line (e.g., DFCI032 cell line (adenocarcinoma); H1755 cell line (neuroendocrine)), using, for example, the Maxwell Promega blood kit #AS1400, as described above. The DNA is bisulfite converted, e.g., as described above.

A pre-amplification is conducted, for example, in a reaction mixture containing 7.5 mM $MgCl_2$, 10 mM MOPS, 0.3 mM Tris-HCl, pH 8.0, 0.8 mM KCl, 0.1 μg/μL BSA, 0.0001% Tween-20, 0.0001% IGEPAL CA-630, 250 μM each dNTP, oligonucleotide primers, (e.g., for 12 targets, 12 primer pairs/24 primers, in equimolar amounts (including but not limited to the ranges of, e.g., 200-500 nM each primer), or with individual primer concentrations adjusted to balance amplification efficiencies of the different target regions), 0.025 units/μL HotStart GoTaq concentration, and 20 to 50% by volume of bisulfite-treated target DNA (e.g., 10 μL of target DNA into a 50 μL reaction mixture, or 50 μL of target DNA into a 125 μL reaction mixture). Thermal cycling times and temperatures are selected to be appropriate for the volume of the reaction and the amplification vessel. For example, the reactions may be cycled as follows

| Stage | Temp/Time | #of Cycles |
|---|---|---|
| Pre-incubation | 95° C./5' | 1 |
| Amplification 1 | 95° C./30"<br>64° C./30"<br>72° C./30" | 10-12 |
| Cooling | 4° C./Hold | 1 |

After thermal cycling, aliquots of the pre-amplification reaction (e.g., 10 μL) are diluted to 500 μL in 10 mM Tris, 0.1 mM EDTA, with or without fish DNA. Aliquots of the diluted pre-amplified DNA (e.g., 10 μL) are used in a QuARTS PCR-flap assay, e.g., as described above. See also U.S. Patent Appl. Ser. No. 62/249,097, filed Oct. 30, 2015; application Ser. No. 15/335,096, filed Oct. 26, 2016, and PCT/US16/58875, filed Oct. 26, 2016, and U.S. Pat. No. 10,648,025, each of which is incorporated herein by reference in its entirety for all purposes.

The present technology is not limited to use of flap endonuclease assays, and in different embodiments, any method of analyzing the bisulfite-converted DNA may be used. For example, in some embodiments, the analysis comprises direct sequencing, pyrosequencing, methylation-sensitive single-strand conformation analysis (MS-SSCA), high resolution melting analysis, methylation-sensitive single-nucleotide primer extension (MS-SnuPE), base-specific cleavage/mass spectrometry (e.g., by MALDI-TOF), methylation-specific PCR (MSP), microarray analysis, restriction digest analysis), INVADER assay, combined bisulfite restriction analysis, or methylated DNA immunoprecipitation (MeDIP). These and other methods are reviewed in more detail in, e.g., Fraga M F & Esteller M (2002), "DNA methylation: a profile of methods and applications", *BioTechniques* 33(3): 632, 634, 636-49; El-Maarri O (2003), "Methods: DNA methylation", *Advances in Experimental Medicine and Biology* 544: 197-204; Laird P W (2003), "The power and the promise of DNA methylation markers", *Nat. Rev. Cancer* 3(4): 253-66; Callinan P A & Feinberg A P (2006), "The emerging science of epigenomics", *Hum Mol Genet* 15(90001): R95-101, which are all incorporated by reference in their entireties for all purposes.

EXPERIMENTAL

Example 1

Effect of Binding pH on Recovery of Bisulfite-Converted DNA

In the example described below, single stranded DNA template was sulfonated with ammonium bisulfite (ABS) as described in the exemplary Sulfonation steps, above. Following sulfonation of the DNA, the sulfonation reaction solution was removed by size exclusion filtration and the sulfonated DNA was combined with potassium acetate (KOAc) at low (19 mM K+), middle (228 mM K+) and high (474 mM K+) concentrations. As a control, a portion of the sulfonated DNA template was returned to a bisulfite solution instead of potassium acetate.

Each sample was subsequently incubated with chaotrope and silica beads to promote binding. Table 1 below demonstrates that bisulfite solution inhibited the binding reaction due to high salt concentration for each template. Binding pH was 4.8 to 4.9.

TABLE 1

DNA strands and binding salts

| | | | FAM_NDRG4 | | HEX_BMP3 | | Quasar_BTACT | | |
|---|---|---|---|---|---|---|---|---|---|
| Salt | Cation | Anion | Median | CV | Median | CV | Median | CV | N |
| KOAc | 19 mM | 29 mM | 2617 | 17 | 1053 | 12 | 11106 | 33 | 12 |
| | 228 mM | 610 mM | 1229 | 14 | 535 | 12 | 7837 | 16 | 12 |
| | 474 mM | 2118 mM | 71 | 14 | 17 | 33 | 530 | 21 | 12 |
| ABS | 940 mM | 940 mM | 1772 | 9 | 659 | 9 | 10997 | 15 | 12 |

Six DNA templates (markers) of varying cytosine content (see Table 2, below) were bisulfite-treated, then bound to silica using binding solutions having pHs ranging from 5.0 to 3.4.

TABLE 2

Percent Converted Cytosines of 6 Different Methylation Marker DNA strands

| Test DNA strand | % Converted Cytosines |
|---|---|
| LASS4-Antisense | 33 |
| PPP2R5C-Antisense | 20 |
| ZDHHC1-Antisense | 22 |
| NDRG4-Sense | 37 |
| BMP3-Sense | 36 |
| BTACT-Sense | 16 |

Figure 3:
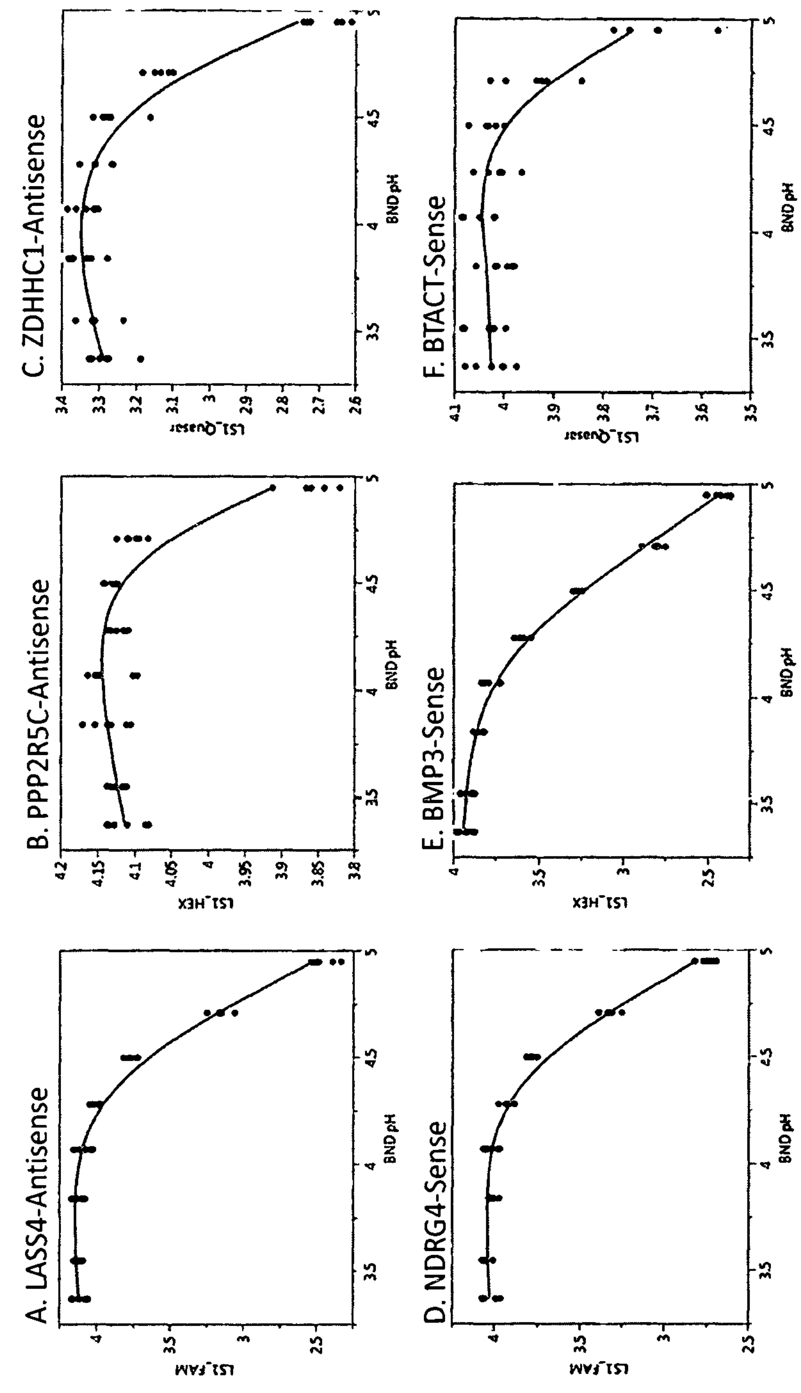
FIG. 3 provides graphs of binding pH vs. log strands recovered for six different marker DNAs.

Results are shown in FIG. 3. The pH required for maximum log strand recovery varied for each marker and appears to correlate with percent converted cytosine (i.e., the percent of total nucleotides in a strand that are unmethylated cytosine nucleotides prior to treatment, and that are uracil sulfonate nucleotides at the binding step) of the sequence. DNAs that have a high content of unmethylated cytosines, and that therefore have a high content of bases converted to uracil sulfonate at the binding step, required lower pH for maximum strand recovery.

Figure 4:
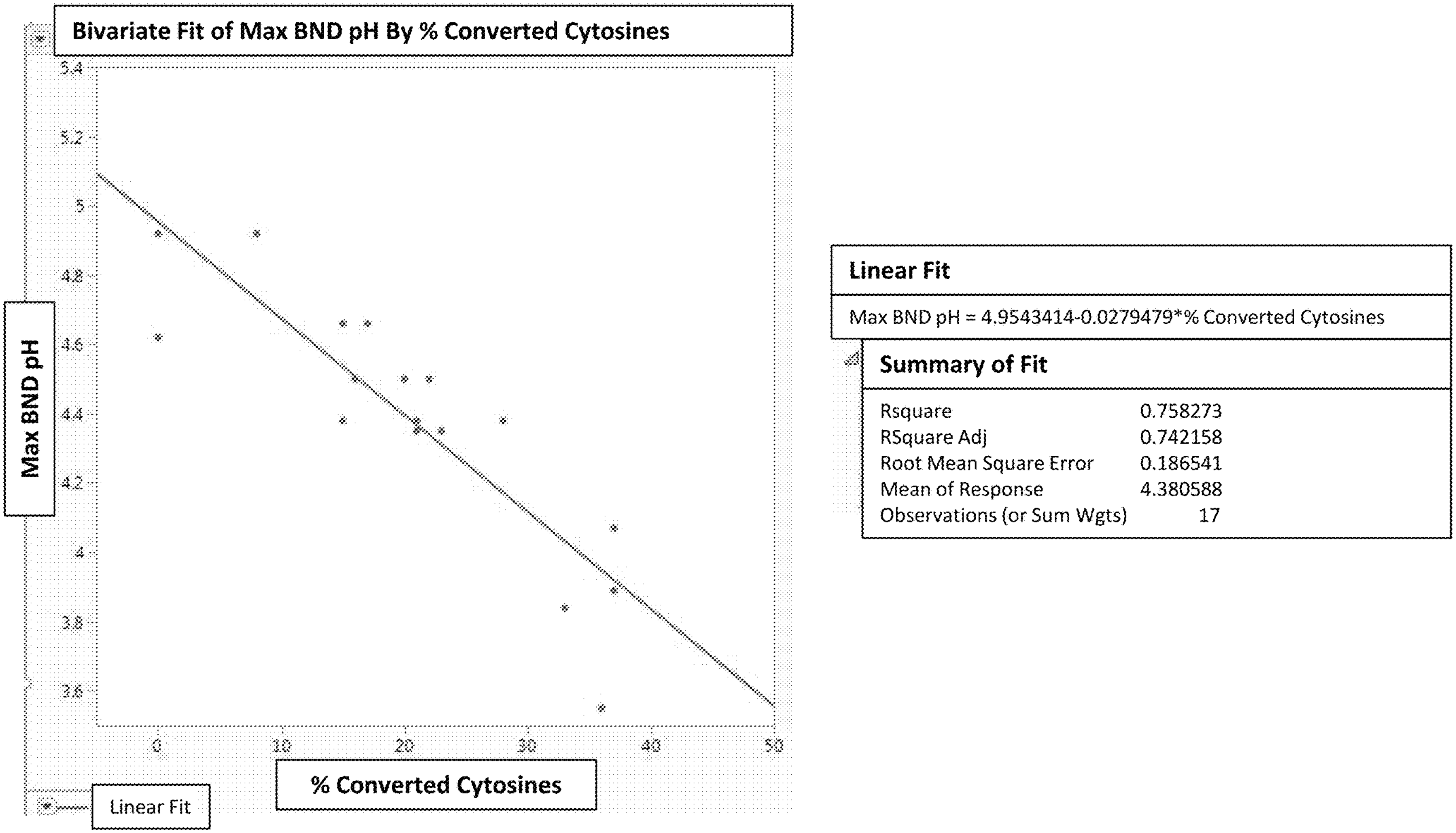
FIG. 4 is a graph of percent converted cytosines vs. maximum binding pH. The percent converted cytosines of each DNA strand (uracil sulfonate nucleotides/total nucleotides) was plotted against the highest estimated binding pH required for maximum strand recovery. A linear fit of these points is shown.

A total of seventeen different DNA sequences were tested in the same manner above. The percent converted cytosines of each DNA was plotted against the highest estimated binding pH required for maximum strand recovery. A linear fit of these points (FIG. 4) had an $R^2$ of 0.76, suggesting the relationship between percent converted cytosines and binding pH was strong.

Figure 5:
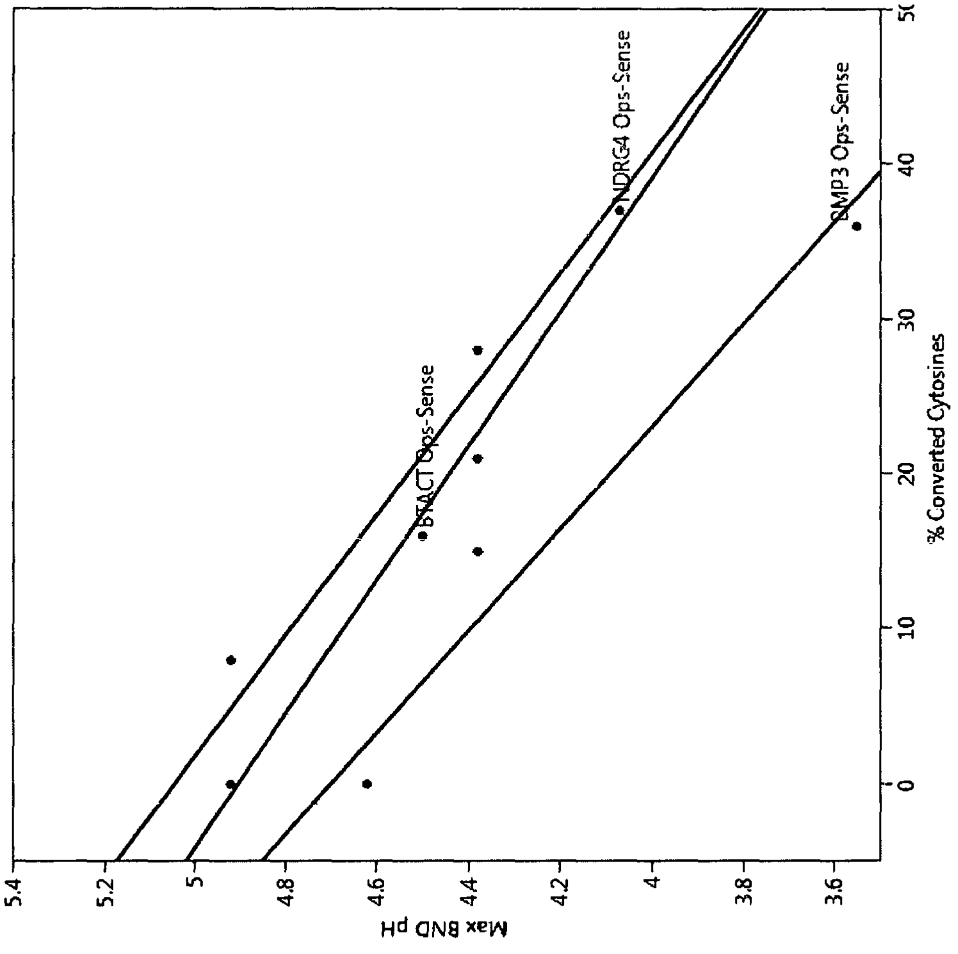
FIG. 5 is a graph of percent converted cytosines vs. maximum binding pH of DNA strands that use the same primer/probe combinations. Three of the DNAs (BMP3, β-actin ("BTACT"), and NDRG4 strands), were modified to produce sets of DNAs that retained the same primer and probe binding sequences for each variant of a particular DNA, but that contained different numbers of unmethylated Cs in other regions of that DNA strand. To further illustrate the strength of this correlation, lines were fit to each set of sequences.

To further illustrate the strength of the correlation between percent converted cytosines and binding pH, three of the DNA strands from FIG. 3 (BMP3, β-actin (bisulfite treated actin, or "BTACT"), and NDRG4), were modified to produce sets of DNAs that retain the same primer and probe binding sequences for each test sequence, but that have different numbers of unmethylated Cs in other regions of that sequence. Lines were fit to captured strand measurements for each set of sequences (FIG. 5). Slopes and intercepts for all four fits (FIGS. 4 and 5) were similar.

Comparison of DNA Sample Types

Strand recovery from binding reactions conducted at low pH (citrate buffer) and at non-adjusted pH (standard conditions) were compared for multiple sample types: single-stranded 126-mer strands of synthetic DNA ("126"), DNA isolated from stool samples spiked with purified cell line DNA ("ECLD"), and DNA isolated from stool samples previously characterized as giving high signal for methylated DNA ("HMS"), with 6 replicates for each combination of sample type and binding condition, with Table 3, below, showing strand recovery results. All DNA from stool samples was isolated with the capture process described above, and the synthetic 126-mer DNA strands were combined with exogenous fish DNA as carrier.

TABLE 3

| % conv. C: (126-mers) | | 15 Strands_LASS4 | | | 17 Strands_LRRC4 | | | 23 Strands_SDC2 | | |
|---|---|---|---|---|---|---|---|---|---|---|
| Samp. Type | Bind pH | Median | Low/ Std. | CV | Median | Low/ Std. | CV | Median | Low/ Std. | CV |
| 126 | Std. | 1081 | 0.94 | 6 | 3366 | 0.89 | 3 | 2179 | 1.38 | 19 |
| 126 | Low | 1020 | | 11 | 2996 | | 4 | 3001 | | 6 |
| Stool + ECLD | Std. | 1034 | 0.96 | 10 | 6307 | 0.92 | 3 | 1809 | 1.18 | 11 |
| Stool + ECLD | Low | 988 | | 9 | 5817 | | 9 | 2137 | | 7 |
| HMS | Std. | 97 | 1.12 | 11 | 143 | 1.09 | 9 | 97 | 1.23 | 16 |
| HMS | Low | 109 | | 9 | 156 | | 8 | 119 | | 3 |

| % conv. C: (126mers) | | 37 Strands_PPP2R5C | | | 21 Strands_ZDHHC1 | | |
|---|---|---|---|---|---|---|---|
| Samp. Type | Bind pH | Median | Low/ Std. | CV | Median | Low/ Std. | CV |
| 126 | Std. | 590 | 2.71 | 26 | 6398 | 1.15 | 19 |
| 126 | Low | 1599 | | 5 | 7354 | | 7 |
| Stool + ECLD | Std. | 525 | 5.00 | 9 | 2707 | 1.82 | 30 |
| Stool + ECLD | Low | 2623 | | 7 | 4931 | | 13 |
| HMS | Std. | 43 | 2.43 | 19 | 12891 | 1.30 | 25 |
| HMS | Low | 104 | | 8 | 16698 | | 12 |

The results in Table 3 show that use of low pH binding reactions produced similar or enhanced strand recovery for each of these sample types.

Surrogate blood samples comprising low (1×) or high (10×) nucleosome matrix were prepared. Nucleosomal DNA was prepared from HCT116 cells using the Active Motif Nucleosome Kit (Active Motif, catalog number 53504.) To mimic methylated DNA marker (MDM)-positive plasma samples, nucleosomal DNA was spiked into pooled plasma collected from healthy donors using LBgard® blood tubes (Exact Sciences, Inc.) or was spiked into SERACON negative diluent. Use of the nucleosome matrix preparation ensures that the MDM-positive DNA has a similar size distribution as that which would be expected in a sample from a cancer-positive patient.

The samples were treated to extract DNA using the plasma extraction procedure described above, or using QIASYMPHONY DSP Circulating DNA kit (Qiagen, Inc.). The extracted DNA samples were then bisulfite-treated and bound at standard (non-adjusted pH) binding reactions as described above (7 M GuHCl binding buffer added to the ABS reaction), and in low pH binding reactions (7 M GuHCl with 133 mM citrate buffer, pH 2.2 binding buffer).

A comparison of 14 DNAs showed increased strand recovery for 15/34 conditions when compared with a t-test (Tables 4, 5, 6 and 7, below). Overall, low binding pH increased strand recovery for a variety of sample types.

TABLE 4

| 10X Nucleosome | | | | | | | |
|---|---|---|---|---|---|---|---|
| Marker | N | Low pH Mean Strands | High pH Mean Strands | Low pH CV Strands | High pH CV Strands | % Diff | p-Value |
| ANKRD13B | 16 | 71137 | 69161 | 11.01 | 9.9 | 2.8 | 0.45 |
| CHST2 | 16 | 91324 | 80004 | 4.97 | 7.5 | 13.2 | 0.00 |

TABLE 4-continued

| 10X Nucleosome | | | | | | | |
|---|---|---|---|---|---|---|---|
| Marker | N | Low pH Mean Strands | High pH Mean Strands | Low pH CV Strands | High pH CV Strands | % Diff | p-Value |
| CNNM1 | 16 | 74580 | 70714 | 11.51 | 9.3 | 5.3 | 0.16 |
| DTX1 | 16 | 52188 | 39531 | 9.19 | 5.6 | 27.6 | 0.00 |
| FER1L4 | 16 | 84883 | 78712 | 8.73 | 11.1 | 7.5 | 0.04 |
| GRIN2D | 16 | 13132 | 12499 | 8.50 | 11.1 | 4.9 | 0.17 |
| JAM3 | 16 | 88788 | 86144 | 7.93 | 9.4 | 3.0 | 0.33 |
| PDGFD | 16 | 32517 | 29745 | 9.49 | 11.4 | 8.9 | 0.02 |
| SFMBT2 | 16 | 79580 | 47298 | 8.34 | 10.2 | 50.9 | 0.00 |
| ZNF568 | 16 | 65277 | 61019 | 6.61 | 6.7 | 6.7 | 0.01 |
| ZNF671 | 16 | 48629 | 42437 | 10.87 | 9.8 | 13.6 | 0.00 |

TABLE 5

| 1X Nucleosome | | | | | | | |
|---|---|---|---|---|---|---|---|
| Marker | N | Low pH Mean Strands | High pH Mean Strands | Low pH CV Strands | High pH CV Strands | % Diff | p-Value |
| ANKRD13B | 16 | 7927 | 7756 | 12.02 | 10.9 | 2.2 | 0.5949 |
| CHST2 | 16 | 12553 | 11796 | 14.64 | 18.2 | 6.2 | 0.2922 |
| CNNM1 | 16 | 10242 | 8732 | 10.61 | 9.4 | 15.9 | 0.0001 |
| DTX1 | 16 | 5933 | 4768 | 12.14 | 15.3 | 21.8 | 0.0001 |
| FER1L4 | 16 | 9949 | 9123 | 10.50 | 10.6 | 8.7 | 0.0271 |
| GRIN2D | 16 | 1599 | 1547 | 22.97 | 17.3 | 3.3 | 0.6472 |
| JAM3 | 16 | 10363 | 9786 | 8.71 | 7.7 | 5.7 | 0.0585 |
| PDGFD | 16 | 4301 | 4039 | 21.10 | 18.6 | 6.3 | 0.3814 |
| SFMBT2 | 16 | 9965 | 5531 | 11.83 | 20.9 | 57.2 | 0.0001 |
| ZNF568 | 16 | 7891 | 7369 | 13.06 | 12.3 | 6.8 | 0.1391 |
| ZNF671 | 16 | 6366 | 5414 | 15.13 | 17.4 | 16.2 | 0.0082 |

TABLE 6

| 10X Nucleosome - Two Extraction Methods | | | | | | | | |
|---|---|---|---|---|---|---|---|---|
| Marker | Extraction | N | Low pH Mean Strands | High pH Mean Strands | Low pH CV Strands | High pH CV Strands | % Diff | p-Value |
| QKI | EXAS | 8 | 22711 | 22547 | 9.8 | 4.1 | 0.7 | 0.8499 |
| VAV3 | EXAS | 8 | 42778 | 47275 | 10.5 | 10.4 | 10.0 | 1.000 |
| ZFRASSF1 | EXAS | 8 | 81016 | 77035 | 6.9 | 7.5 | 5.0 | 0.185 |
| QKI | QIAS | 8 | 30742 | 29806 | 9.8 | 11.8 | 3.1 | 0.5767 |
| VAV3 | QIAS | 8 | 69105 | 63961 | 16.2 | 12.9 | 7.7 | 0.3144 |
| ZFRASSF1 | QIAS | 8 | 104780 | 95303 | 10.5 | 12.3 | 9.5 | 0.1179 |

TABLE 7

| 1X Nucleosome - Two Extraction Methods | | | | | | | | |
|---|---|---|---|---|---|---|---|---|
| Marker | Extraction | N | Low pH Mean Strands | High pH Mean Strands | Low pH CV Strands | High pH CV Strands | % Diff | p-Value |
| QKI | EXAS | 8 | 2731 | 2764 | 10.8 | 13.3 | 1.2 | 1.000 |
| VAV3 | EXAS | 8 | 6181 | 6973 | 24.8 | 22.8 | 12.0 | 1.000 |
| ZFRASSF1 | EXAS | 8 | 94813 | 83699 | 9.8 | 8.1 | 12.5 | 0.016 |
| QKI | QIAS | 8 | 3616 | 3398 | 14.4 | 11.4 | 6.2 | 0.3574 |
| VAV3 | QIAS | 8 | 10329 | 7984 | 14.1 | 14.3 | 25.6 | 0.003 |
| ZFRASSF1 | QIAS | 8 | 113563 | 91078 | 7.7 | 10.5 | 22.0 | 0.0002 |

DNA Isolated from Clarified Supernatant from Stool Samples

Figures 6A, 6B:
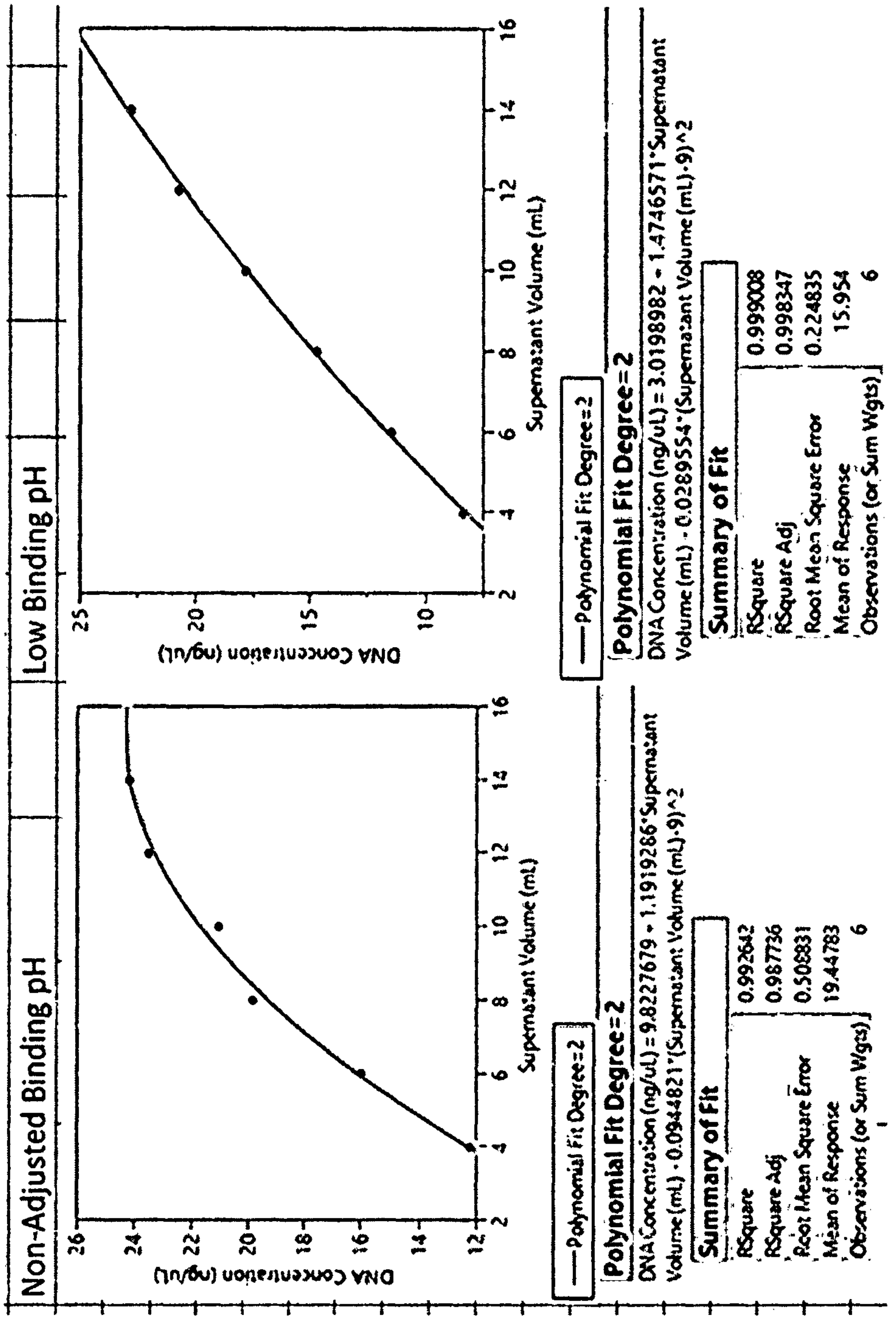
FIGS. 6A and 6B show graphs of total DNA post conversion and clean-up using a non-adjusted binding pH (FIG. 6A) or low binding pH (FIG. 6B).

Cell line DNA-spiked stool samples with sample input volumes ranging from 4 to 14 mLs (standard) were treated to capture the cell line DNA, which was then bisulfate-treated and isolated using standard pH (FIG. 6A) and low binding pH binding (FIG. 6B) solutions. Comparison of FIGS. 6A and 6B shows improved linearity of total DNA and strand recovery with low binding pH. The samples used for non-adjusted (standard) and low binding pH had differing amounts of DNA templates spiked in thus, total strand recoveries shown should not be directly compared across binding conditions.

Figure 7:
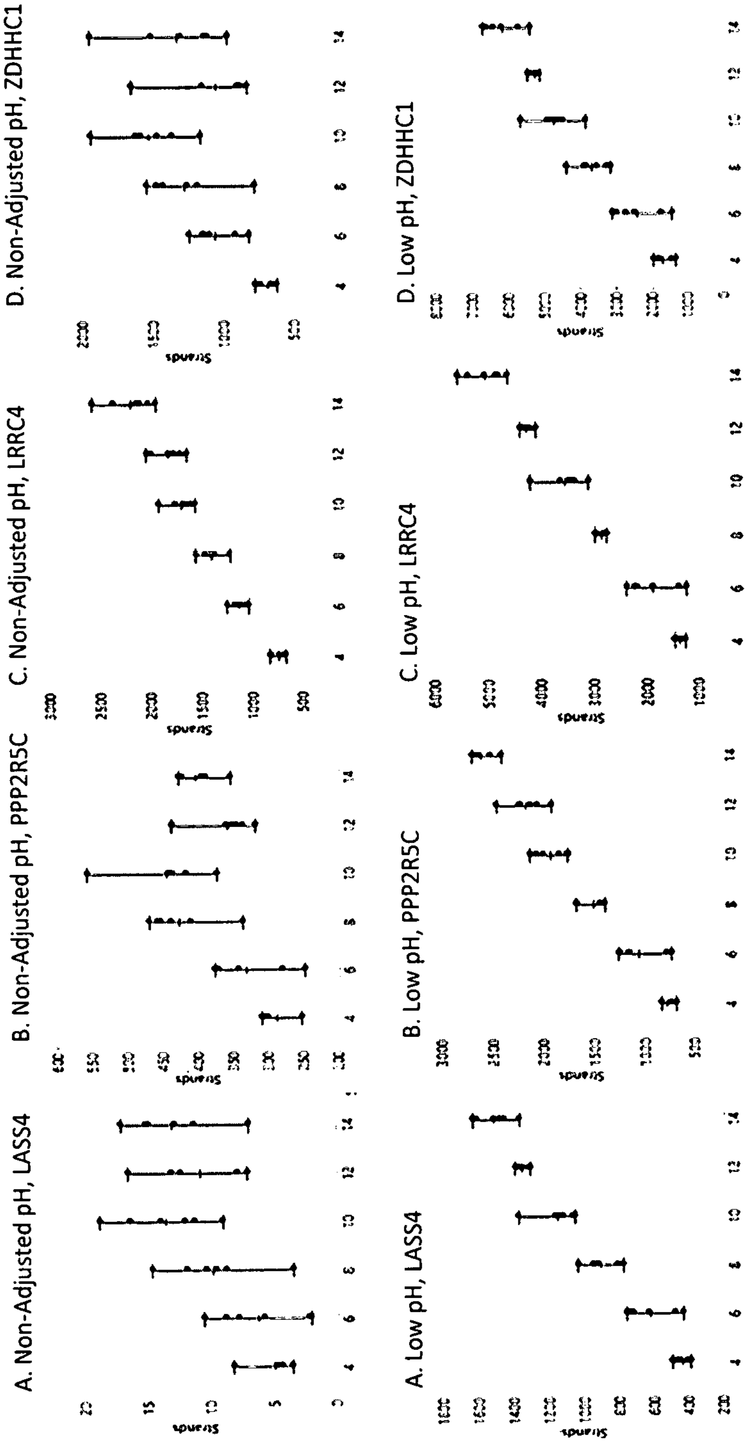
FIG. 7 are graphs of stool sample volume (mLs) versus strands recovered for a non-adjusted binding pH (top row) or low binding pH (bottom row) for four different DNA sequences (LASSO, PPP2R5C, LRRC4, and ZDHHC1). The ZDHHC1 DNAs were tested twice.

The amount of DNA recovered from each volume of stool sample (mLs) using non-adjusted or low pH binding conditions is shown in the eight panels of FIG. 7.

Effect of Different Lots of Ammonium Bisulfite

Four ammonium bisulfite (56%) lots were tested side-by-side with non-adjusted and low binding pH conditions. The ABS lots varied in age; the oldest was nine years old and had the lowest pH, ammonium bisulfite can degrade as much as two percentage points per year. Without pH adjustment strand recovery varied across lots where the oldest material had the highest recovery (FIG. 8A). With low binding pH, the recovery alignment improved.

Effect of Ammonium Bisulfite Concentration

Ammonium bisulfite was titrated from 57 to 43% concentration, then tested with synthetic DNA templates bound with low binding pH (citric acid buffer) or with no pH adjustment. Using the 56.6% as the reference value, the % difference in binding for the lower ABS concentrations were calculated for each of the indicated markers DNA. Results are shown in the table in FIG. 8B. Strand recovery alignment across ABS concentrations improved with low binding pH.

An unknown binding solution (7 M guanidine-HCl) contaminant introduced during manufacturing was found to suppress the recovery of select markers. When low binding pH and non-adjusted strand recovery were compared with and without the contaminant, the low binding pH conditions reduced the drop in recovery compared to the non-adjusted binding conditions. (FIG. 9).

Recovery using Different Manufacturers' Beads

Silica beads from multiple vendors were tested for use in bisulfite conversion with non-adjusted pH at binding or with low binding pH, with results are shown in FIGS. 10 and 11, respectively. Some beads showed no strand recovery at unadjusted binding pH (FIG. 10), but showed improved recovery with lowered binding pH (FIG. 11). Bead concentrations were not adjusted to be equal for initial screenings in FIG. 10, but were aligned for the testing shown in FIG. 11.

DNA Recovery Across a pH Range

Acidic conditions can cause loss in strand recovery due to acid hydrolysis of DNA template. When binding pH was examined over the range from 4.9 to 2.1, strand recovery was most consistent from about pH 3.9 to around 2.5 (see FIG. 12).

Effect of DNA Size and Concentration

DNA size and concentration can vary across and within sample types such as tissue, blood, and stool. In this experiment calf thymus DNA was titrated to 300, 2700, and 5400 ng/ran at sizes of 200 bp, 3.6 reaction, and 20 kbp. DNA samples were spiked with 126 bp synthetic target molecules, and were treated with bisulfite using with non-adjusted binding pH and low binding pH for capture of the sulfonated DNA. Results are shown in FIG. 13.

As DNA size decreased and concentration increased, strand recovery was significantly reduced with non-adjusted binding pH chemistry. Strand recovery with low binding pH chemistry was greatly improved over non-adjusted binding pH (as much as 374%). Additionally, the coefficients of variation (CVs) were improved with low binding pH chemistry.

Example 2

Comparison of Three Binding Protocols

In the following example, three different procedures for binding sulfonated DNA to silica are compared.

Protocol 1 is a standard protocol in which the sulfonation reaction is combined with a binding solution of 7 M guanidine hydrochloride (GuHCl), but no acid is added to reduce the pH.

In Protocol 2, the sulfonation reaction mixture is combined with a binding solution of 7 M GuHCl, 133 mM Citrate, pH 2.2.

In Protocol 3, the sulfonation reaction mixture is combined with a binding solution of 7 M GuHCl, but no acid is added to reduce the pH.

In each of the procedures described, the bead-bound sulfonated DNA is desulfonated on the solid support, as described, e.g., in U.S. Pat. No. 9,315,853, which is incorporated herein by reference in its entirety.

Conversion protocols are described below for performance on Hamilton STARlet automatic pipetting system, but can be performed manually with equivalent equipment.

Protocol 1

This procedure describes processing of DNA captured from a sample, e.g., a stool sample, using sequence-specific capture beads that comprise a capture oligonucleotide complementary to the target DNA.

Denaturation:

1. To washed capture bead pellets, add 20 μL of 90 ng/μL, BSA, 10 mM Tris pH 8.0, 1 mM EDTA and 160 μL of 100 mM NaOH.
2. Incubate at 43 °C with 1500 RPM mixing for 45 seconds.
3. Incubate an additional 19 minutes, 15 seconds at 43 °C without mixing (20 minutes total).
4. Bind on magnet for 5 minutes.
5. Transfer 80 μL of denatured sample to new deep well plate.

Sulfonation:

1. Add 120 μL of 57% wt/wt ammonium bisulfite (ABS) to denatured sample.
2. Place on heater shaker at 65.5 °C with 1200 RPM mixing for 3 minutes.
3. Incubate for an additional 72 minutes without mixing (75 minutes total).

Sulfonated DNA Binding:

1. Add 750 μL of 7 M GuHCl binding solution to samples.
2. Mix bead stock for 5 cycles via pipette and add 50 μL 16 mg/mL paramagnetic silica beads to each sample.
3. Incubate 30 minutes at 30.5 °C with 1200 RPM mixing.
4. Place on magnet for 5 minutes to bind beads, aspirate supernatant to waste.

Alcohol Washes 1 and 2:

1. Add 1 mL 80% ethanol (EtOH), 10 mM Tris pH 8.0 conversion wash to bead pellets.
2. Mix for 3 minutes at 1200 RPM.
3. Place on magnet for 5 minutes to bind beads, aspirate supernatant to waste.

4. Add 250 μL 80% EtOH, 10 mM Tris pH 8.0 conversion wash to bead pellets.
5. Mix for 3 minutes at 1200 RPM.
6. Place on magnet for 2 minutes to bind beads, aspirate supernatant to waste.

Desulfonation:

1. Add 200 μL of 70% isopropyl alcohol (IPA), 105 mM NaOH to bead pellets.
2. Incubate at 30.5 °C with 1200 RPM mixing for 7 minutes.
3. Place on magnet for 2 minutes to bind beads, aspirate supernatant to waste.

Alcohol Washes 3 and 4:

1. Add 250 μL, 80% EtOH, 10 mM Tris pH 8.0 conversion wash to bead pellets.
2. Mix for 3 minutes at 1200 RPM.
3. Place on magnet for 2 minutes to bind beads, aspirate supernatant to waste.
4. Add 250 μL 80% EtOH, 10 mM Tris pH 8.0 conversion wash to bead pellets.
5. Mix for 3 minutes at 1200 RPM.
6. Place on magnet for 2 minutes to bind beads, aspirate supernatant to waste.

Dry Beads and Elute DNA:

1. Incubate bead pellets at 71.5 °C with 1200 RPM mixing for 15 minutes to dry.
2. Add 70 μL of 10 mM Tris pH 8.0, 0.1 mM EDTA to dry beads.
3. Incubate at 66.5 °C with 1200 RPM mixing for 25 minutes.
4. Place on magnet for 8 minutes to cool and bind beads.
5. Converted DNA is ready for assays.

Protocol 2

This procedure describes processing of DNA captured from a sample, e.g., a stool sample, using sequence-specific capture beads that comprise a capture oligonucleotide complementary to the target DNA.

Denaturation:

1. To washed capture bead pellets, add 50 μL of 36 ng/μL BSA, 10 mM Tris pH 8.0, 1 mM EDTA and 50 μL 160 mM NaOH.
2. Incubate at 32.5 °C with 1500 RPM mixing for 3 minutes.
3. Bind on magnet for 5 minutes.
4. Transfer 80 μL of denatured sample to new deep well plate.

Sulfonation:

1. Add 120 μL of 52% wt/wt ABS to denatured sample.
2. Place on heater shaker at 62.5 °C with 1200 RPM mixing for 3 minutes.
3. Incubate for an additional 85 minutes without shaking (88 minutes total).

Sulfonated DNA Binding:

1. Add 750 μL of 7 M GuHCl, 133 mM Citrate, pH 2.2 binding solution to samples.
2. Mix bead stock for 5 cycles via pipette and add 50 μL 16 mg/mL paramagnetic silica beads to each sample.
3. Incubate 15 minutes at 32.5 °C with 1200 RPM mixing:
4. Place on magnet for 5 minutes to bind beads, aspirate supernatant to waste.

Alcohol Washes 1 and 2:

1. Add 1 mL 75% IPA, 20 mM Tris pH 7.8 conversion wash to bead pellets.
2. Mix for 3 minutes at 1200 RPM.
3. Place on magnet for 5 minutes to bind beads, aspirate supernatant to waste.
4. Add 250 μL 75% IPA, 20 mM Tris pH 7.8 conversion wash to bead pellets.
5. Mix for 3 minutes at 1200 RPM.
6. Place on magnet for 2 minutes to bind beads, aspirate supernatant to waste.

Desulfonation:

1. Add 200 μL of 70% IPA, 30 mM NaOH to bead pellets.
2. Incubate at 32.5 °C with 1200 RPM mixing for 3 minutes.
3. Place on magnet for 2 minutes to bind beads, aspirate supernatant to waste.

Alcohol Washes 3 and 4:

1. Add 250 μL 75% IPA, 20 mM Tris pH 7.8 conversion wash to bead pellets.
2. Mix for 3 minutes at 1200 RPM.
3. Place on magnet for 2 minutes to bind beads, aspirate supernatant to waste.
4. Add 250 μL 75% IPA, 20 mM Tris pH 7.8 conversion wash to bead pellets.
5. Mix for 3 minutes at 1200 RPM.
6. Place on magnet for 2 minutes to bind beads, aspirate supernatant to waste.

Dry Beads and Elute DNA:

1. Incubate bead pellets at 71.5 °C with 1200 RPM mixing for 15 minutes to dry.
2. Add 70 μL of 3 mM Tris pH 7.8, 0.1 mM EDTA to dry beads.
3. Incubate at 66.5 °C with 1200 RPM mixing for 25 minutes.
4. Place on magnet for 25 minutes to cool and bind beads.
5. Converted DNA is ready for assays.

Protocol 3

This procedure describes processing of DNA extracted from a sample, e.g., from plasma, using chaotrope-mediated binding to a silica support. The DNA is eluted from the support prior to the denaturation step below.

Denaturation:

1. To 75 μL of extracted DNA sample, add 11 μL of 90 ng/μL BSA, 10 mM Tris pH 8.0, 1 mM EDTA and 11 μL of 1.0 M NaOH.
2. Incubate at RT with 1200 RPM mixing for 1 minute.

Sulfonation:

1. Add 120 μL of 52% wt/wt ABS to denatured sample.
2. Place on heater shaker at 65.5 °C with 1200 RPM mixing for 3 minutes.
3. Incubate for an additional 72 minutes without mixing (75 minutes total).

Sulfonated DNA Binding:

1. Add 750 μL of 7 M GuHCl binding solution to samples.
2. Mix bead stock for 5 cycles via pipette and add 50 μL 16 mg/mL paramagnetic silica beads to each sample.
3. Incubate 30 minutes at 30.5 °C with 1200 RPM mixing.
4. Place on magnet for 5 minutes to bind beads, aspirate supernatant to waste.

Alcohol Washes 1 and 2:

1. Add 1 mL 80% EtOH, 10 mM Tris pH 8.0 conversion wash to bead pellets.
2. Mix for 3 minutes at 1200 RPM.
3. Place on magnet for 5 minutes to bind beads, aspirate supernatant to waste.
4. Add 250 μL 80% EtOH, 10 mM Tris pH 8.0 conversion wash to bead pellets.
5. Mix for 3 minutes at 1200 RPM.
6. Place on magnet for 2 minutes to bind beads, aspirate supernatant to waste.

Desulfonation:

1. Add 200 μL of 75% IPA, 87.5 mM NaOH to bead pellets.
2. Incubate at 30.5 °C with 1200 RPM mixing for 7 minutes.
3. Place on magnet for 2 minutes to bind beads, aspirate supernatant to waste.

Alcohol Washes 3 and 4:

1. Add 250 μL 80% EtOH, 10 mM Tris pH 8.0 conversion wash to bead pellets.
2. Mix for 3 minutes at 1200 RPM.
3. Place on magnet for 2 minutes to bind beads, aspirate supernatant to waste.
4. Add 250 μL 80% EtOH, 10 mM Tris pH 8.0 conversion wash to bead pellets.
5. Mix for 3 minutes at 1200 RPM.
6. Place on magnet for 2 minutes to bind beads, aspirate supernatant to waste.

Dry beads and elute DNA:

1. Incubate bead pellets at 71.5 °C with 1200 RPM mixing for 15 minutes to dry.
2. Add 80 μL of 4 mM Tris pH 8.0, 0.1 mM EDTA to dry beads.
3. Incubate at 66.5 °C with 1200 RPM mixing for 25 minutes.
4. Place on magnet for 20 minutes to cool and bind beads.
5. Converted DNA is ready for assays.

The conditions described above are summarized and compared in the table in FIG. 14.

To compare the treatment protocols described above, genomic DNA was extracted from cell line OE33 cells (esophageal carcinoma) using the MAXWELL system (Promega Corp., Fitchburg, WI), and RSC. Blood DNA Kit (Promega Corp., Cat #ASB1400), both according to manufacturer's instructions. The prepared DNA was used in all 3 protocols, and was added directly to the Denaturation step of each protocol, with no intervening DNA capture step. Strand recoveries for each of Protocols 1, 2, and 3 were tested on DNA at concentrations of 26.7, 17.8, 11.87, 7.91, 5.27, 3.52 ng/μL. Four replicates of each condition were tested. The sequences tested in the prepared DNAs were methylation marker genes ZNF568, BMP3, B3GALT6, NDRG4, VA V3, and ZNF682. Detailed data is shown in FIGS. 15A and 15B.

FIG. 16 shows a table with pairwise comparisons of strand recoveries from Protocol 2 (using low pH binding), compared to Protocol 1 and to Protocol 3 (both with no pH adjustment for binding.), based on the data shown in FIGS. 15A-15B for the different methylation marker DNAs.

Figure 17:
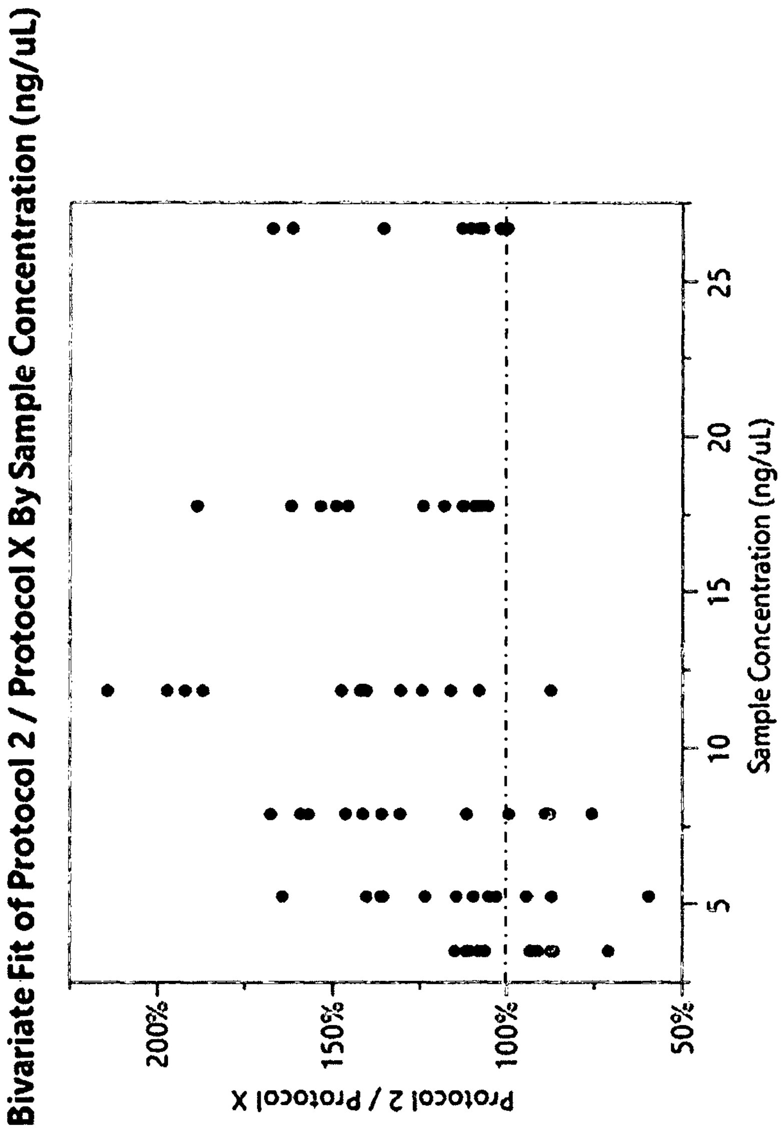
FIG. 17 shows a graph comparing strand recoveries shown in FIG. 16 for different methylation marker DNAs, shown as the ratios of Protocol 2 recovery vs. recovery using Protocol 1 or Protocol 3. "Protocol X" for each datapoint represents either Protocol 1 or 3 for that datapoint.

FIG. 17 shows a graph showing the percentage change using Protocol 2 vs. Protocol 1 or Protocol 3 (collectively grouped as "Protocol X") at the indicated DNA concentrations. The dashed line indicates 100%, i.e., equal recovery using Protocol 2 and Protocol X. Increased strand recovery levels were seen with the Protocol 2 method (which used low pH binding conditions) compared to both of the other two protocols (which both used standard, unadjusted pH binding conditions) with the exception of the VAV3 marker DNA at lower DNA concentrations tested, for which Protocol 1 gave higher strand recovery.

Buffer Comparison

Protocol 2 was used as described above, with the Sulfonated DNA Binding step modified to use glycine, citrate, malate, or formate buffer in the GuHCl binding solution. An unbuffered control reaction used GuHCl with no added buffer at the binding step. The results are shown in FIG. 18.

All literature and similar materials cited in this application, including but not limited to, patents, patent applications, articles, books, treatises, manufacturer's instructions, product enclosures, and interne web pages are expressly incorporated by reference in their entirety for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control.

Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in molecular biology, diagnostics, pharmacology, biochemistry, medical science, or related fields are intended to be within the scope of the following claims.

What is claimed is:

1. A method of binding sulfonated DNA to a silica support, the method comprising combining sulfonated DNA and a silica support in an acidic binding solution comprising a chaotropic salt and an acidic buffer, wherein the pH of the acidic binding solution is 4 or less.

2. The method of claim 1, wherein the silica support comprises one of a particle and a bead.

3. The method of claim 1, wherein the pH of the acidic binding solution is between 2.5 and 4.

4. The method of claim 1, wherein
the acidic buffer comprises a and citrate buffer.

5. The method of claim 1, wherein the method further comprises incubating single-stranded DNA with a sulfonation reagent to produce the sulfonated DNA in a sulfonation reaction solution.

6. The method of claim 5, wherein the sulfonation reagent comprises at least one of ammonium bisulfite and sodium bisulfite.

7. The method of claim 5, further comprising at least one of:

i) separating sulfonated DNA bound to the silica support from the acidic binding solution to produce separated sulfonated DNA; and ii) washing the silica support bound to sulfonated DNA.

8. The method of claim 7, wherein the single-stranded DNA comprises one or more unmethylated cytosine nucleotides.

9. The method of claim 7, further comprising treating separated sulfonated DNA under conditions in which the separated sulfonated DNA is desulfonated to produce desulfonated DNA.

10. The method of claim 2, wherein the silica support comprises one of a magnetic particle and a magnetic bead.

11. The method of claim 1, wherein the chaotropic salt comprises at least one of guanidine hydrochloride (GuHCl) and guanidine isothiocyanate.

12. The method of claim 1, wherein the acidic binding solution is formed by adding the acidic buffer to the sulfonated DNA in a sulfonation reaction solution.

13. The method of claim 9, wherein treating separated sulfonated DNA under conditions comprises combining separated sulfonated DNA with a desulfonation solution.

14. The method of claim 13, wherein the desulfonation solution is combined with separated sulfonated DNA that is bound to the silica support.

15. The method of claim 9, wherein the desulfonated DNA comprises one or more deoxyuracil nucleotides.

16. The method of claim 9, further comprising eluting desulfonated DNA from the silica support.

* * * * *